United States Patent
Ooba et al.

(10) Patent No.: US 7,022,089 B2
(45) Date of Patent: Apr. 4, 2006

(54) ULTRASONIC WAVE COSMETIC DEVICE

(75) Inventors: Takafumi Ooba, Osaka (JP); Masayuki Hayashi, Osaka (JP); Mahito Nunomura, Osaka (JP); Hideaki Abe, Osaka (JP)

(73) Assignee: Matsushita Electric Works, Ltd., Osaka (JP)

(*) Notice: Subject to any disclaimer, the term of this patent is extended or adjusted under 35 U.S.C. 154(b) by 561 days.

(21) Appl. No.: 10/155,709

(22) Filed: May 28, 2002

(65) Prior Publication Data

US 2002/0177792 A1    Nov. 28, 2002

(30) Foreign Application Priority Data

May 28, 2001  (JP) .............................. 2001-159600

(51) Int. Cl.
*A61H 23/00*    (2006.01)

(52) U.S. Cl. .......................................... 601/2; 600/439
(58) Field of Classification Search ................ 601/2–4; 600/439; 606/169; 310/311–324
See application file for complete search history.

(56) References Cited

U.S. PATENT DOCUMENTS

| | | | | |
|---|---|---|---|---|
| 4,081,889 A | * | 4/1978 | Levine ...................... | 29/25.35 |
| 5,186,176 A | * | 2/1993 | Hiki et al. .................. | 600/447 |
| 5,458,130 A | * | 10/1995 | Kaufman et al. ........... | 600/449 |
| 5,460,595 A | * | 10/1995 | Hall et al. ...................... | 601/2 |
| 5,558,623 A | * | 9/1996 | Cody ............................ | 601/2 |
| 6,066,135 A | * | 5/2000 | Honda ......................... | 606/39 |
| 6,183,426 B1 | * | 2/2001 | Akisada et al. ................ | 601/2 |

* cited by examiner

*Primary Examiner*—Brian L. Casler
*Assistant Examiner*—Julianne M. Sullivan
(74) *Attorney, Agent, or Firm*—Muramatsu & Associates

(57) ABSTRACT

An ultrasonic wave cosmetic device for producing ultrasonic wave stimulation on the facial skin by a vibration unit having an ultrasonic wave vibration element. The ultrasonic wave cosmetic device includes a probe provided with a vibration unit where one surface of the vibration unit contacts the skin and another surface is structured by a horn connected to the ultrasonic wave vibration element, and a drive unit for driving the ultrasonic wave vibration element. The drive unit produces one of either a first fundamental frequency where a half-wave length thereof matches a thickness of the vibration unit, which is a sum of the ultrasonic wave vibration element and the horn, when propagating therethrough, or a first harmonic frequency which is an integer multiple of the first fundamental frequency, as a drive frequency for driving the ultrasonic wave vibration element.

19 Claims, 22 Drawing Sheets

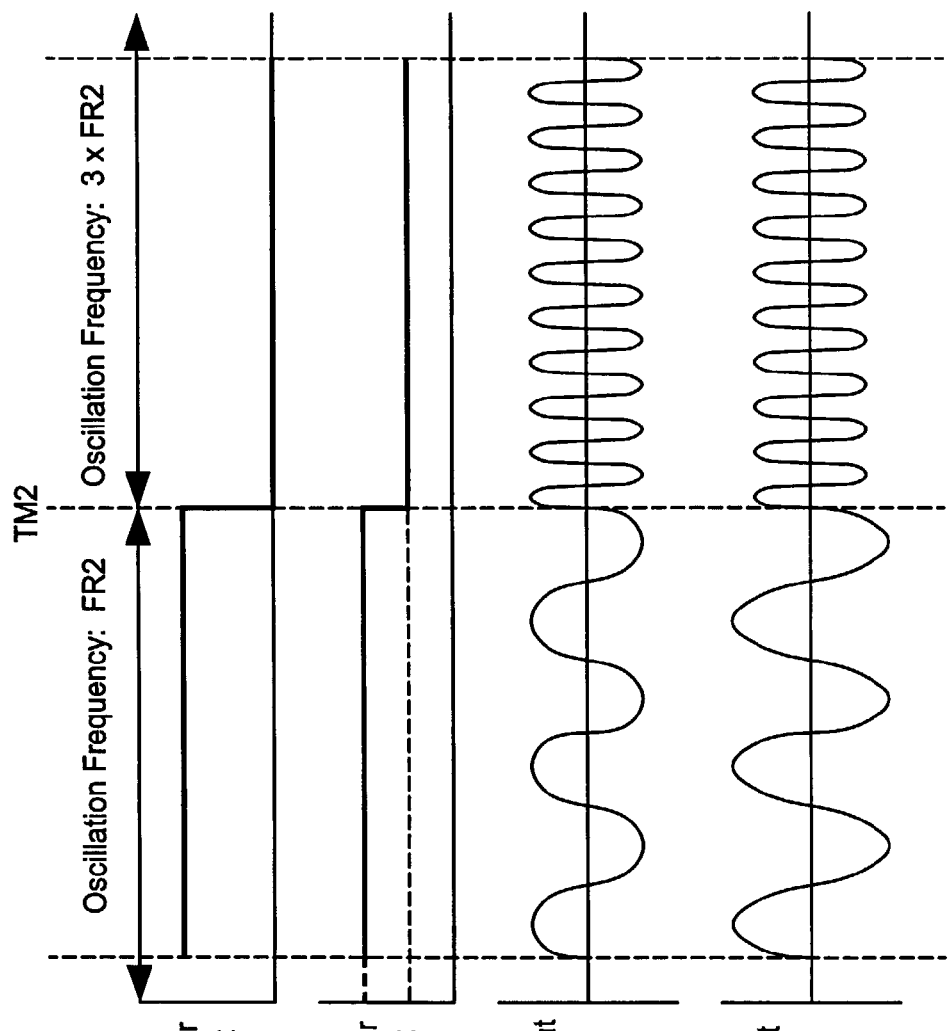

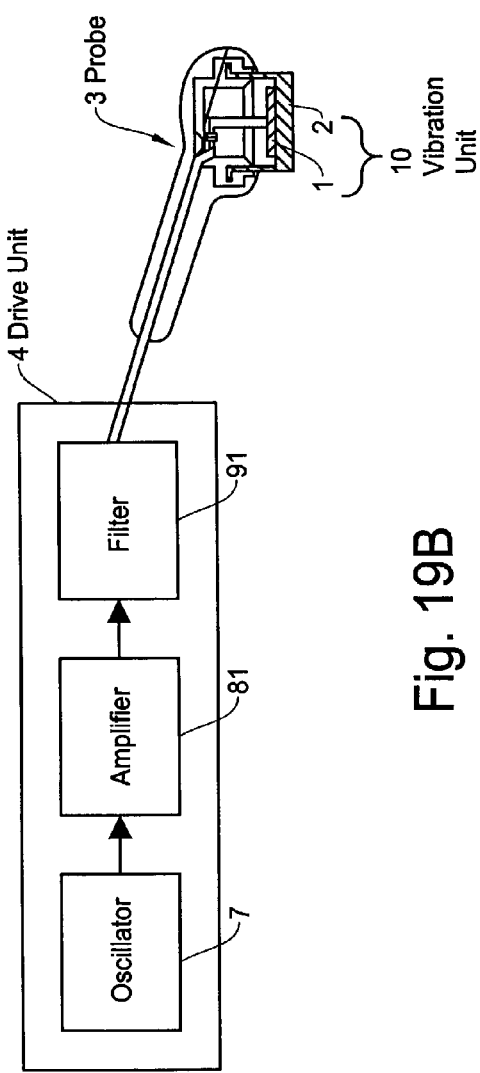
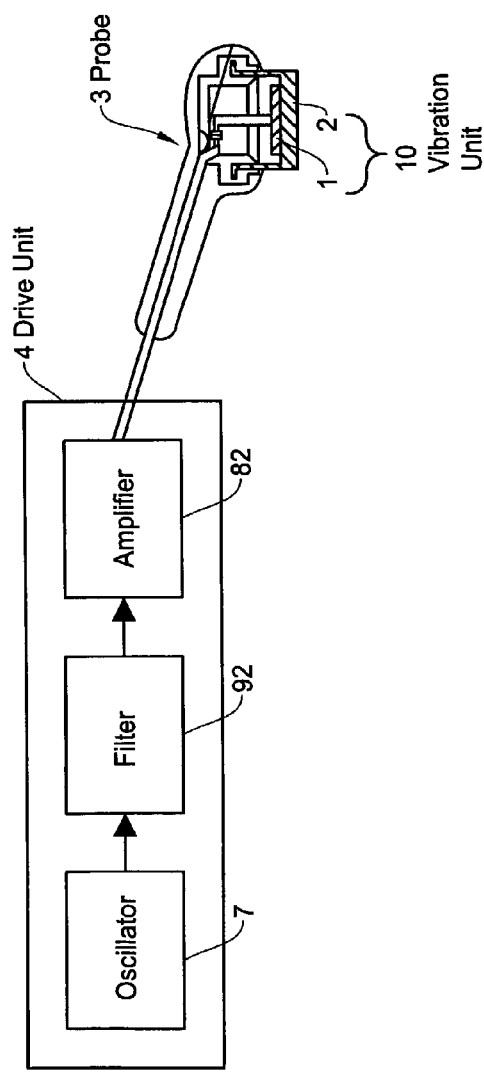

ULTRASONIC WAVE COSMETIC DEVICE

FIELD OF THE INVENTION

The present invention relates to an ultrasonic wave cosmetic device for producing ultrasonic wave stimulation on the facial skin by a vibration unit having an ultrasonic wave vibration element.

BACKGROUND OF THE INVENTION

In recent years, ultrasonic wave cosmetic devices have been used for providing ultrasonic wave vibrations (ultrasonic wave stimulation) to the facial skin by contacting the facial skin with a vibration unit established at a probe head and configured by an ultrasonic wave vibration element and a horn. FIG. 22 is a diagram showing an example of a conventional structure of such an ultrasonic wave cosmetic device. FIG. 22A shows an entire structure of the device, and FIG. 22B shows an enlarged view of a vibration unit 10 descried later.

The ultrasonic wave cosmetic device is comprised of an ultrasonic wave vibration element 1 with a thickness of TH1 for generating ultrasonic waves, a probe 3 having the vibration unit 10 where one surface of the vibration unit contacts with the skin while the other surface is provided with a horn 2 of a thickness TH2 connected to the ultrasonic wave vibration element 1, and a drive unit 4 for driving the ultrasonic wave vibration element 1. The ultrasonic wave vibration element 1 is made of piezoelectric ceramic, and horn 2 is made of aluminum.

FIG. 23 is a diagram showing the ultrasonic wave (standing wave) propagating through the vibration unit 10 in the conventional ultrasonic wave cosmetic device. Here, for convenience, the longitudinal ultrasonic wave is illustrated as a transversal wave. Further, since a wavelength λ of the ultrasonic wave propagating through a medium changes by the speed (sound velocity) of the ultrasonic wave (wavelength=sound velocity/frequency) propagating therethrough, a difference will arise in the wavelength of the ultrasonic wave propagating through the medium with different sound velocity. However, for convenience of explanation, it is assumed that the wavelength λ of the ultrasonic wave is unchanged by the difference of medium. In FIG. 23, the cross section of the vibration unit 10 is shown on the right, and the waveforms of the ultrasonic wave in the vibration unit 10 is shown on the left.

As shown in FIG. 23, in the conventional technology, the thickness TH1 of the ultrasonic wave vibration element 1 and the thickness TH2 of the horn 2 are set to a half-wave length λ/2 and an integer multiple of the half-wave length λ/2 (two times, in this case), respectively. Further, in the ultrasonic wave cosmetic device, an ultrasonic wave with a frequency of 1–3 MHz is used. Thus, the thickness TH1 of the ultrasonic wave vibration element 1 and the thickness TH2 of the horn 2 are respectively, for example, 2 mm and 4 mm, when the frequency is 1 MHz, and 0.7 mm and 1.4 mm, when the frequency is 3 MHz.

Based on the above noted reason, the thickness TH1 of ultrasonic wave vibration element 1 and the thickness TH2 of the horn 2 need to be thinner as the frequency of the ultrasonic wave increases. However, a thinner ultrasonic wave vibration element 1, for example, less than 0.6 mm and a thinner horn 2, for example, less than 1 mm, tend to cause variations in their performances. Further, the performance may change significantly due to, for example, damages resulted from stress caused by the vibrations during use, thus, making it difficult to achieve the desired performance. As a result, a high frequency ultrasonic wave cosmetic device is difficult to achieve in the conventional technology.

Moreover, the vibration unit 10 has to be replaced when using an ultrasonic wave of different frequency, which requires a plurality of vibration units 10 and thus involves a complicated exchange process.

SUMMARY OF THE INVENTION

This invention has been made in view of the above noted problems involved in the conventional technology, and it is an object of the present invention to provide an ultrasonic wave cosmetic device which is capable of using ultrasonic waves with high frequencies.

It is another object of the present invention to provide an ultrasonic wave cosmetic device which is capable of using a plurality of ultrasonic waves with different frequencies.

In the first aspect of the present invention, the ultrasonic wave cosmetic device for providing ultrasonic stimulation to skin is comprised of an ultrasonic wave vibration element for generating ultrasonic waves, a probe provided with a vibration unit where one surface of the vibration unit contacts the skin and another surface is formed of a horn connected to the ultrasonic wave vibration element, and a drive unit for driving the ultrasonic wave vibration element. The drive unit produces at least one of a first fundamental frequency where a half-wave length thereof matches a thickness of the vibration unit (sum of the thickness of the ultrasonic wave vibration element and the horn) when propagating therethrough, and a first harmonic frequency which is an integer multiple of the first fundamental frequency, as a drive frequency for driving the ultrasonic wave vibration element.

According to this structure, since the drive unit produces at least one of the first fundamental frequency and the first harmonic frequency as the drive frequency, it is possible to drive the vibration unit with high frequency as well as with a plurality of frequencies.

In the ultrasonic wave cosmetic device in the second aspect of the present invention, the drive unit produces at least one of a second fundamental frequency, where a half-wave length thereof matches a thickness of the ultrasonic wave vibration element when propagating therethrough, and a second harmonic frequency which is an integer multiple of the second fundamental frequency, as the drive frequency.

According to this structure, since the drive unit produces at least one of the second fundamental frequency or the second harmonic frequency as the drive frequency, the location of the joint surface between the ultrasonic wave vibration element and the horn aligns with the mid-portions of the standing waves, making the stress applied to the joint surface caused by the vibration substantially zero (=0). Hence, there is almost no energy loss, thereby improving the drive efficiency as well as preventing damages such as breakage of the joint surface.

In the ultrasonic wave cosmetic device in the third aspect of the present invention, the drive unit produces at least one of the second fundamental frequency and a third harmonic frequency which is an odd multiple of the second fundamental frequency, as the drive frequency. According to this structure, since one of either the second fundamental frequency or the third harmonic frequency is used as the drive frequency, the displacement of the ultrasonic wave vibration element between the surface facing the horn and the other surface will be in the opposite directions. Due to this, the ultrasonic wave vibration element will mechanically resonate, further improving the drive efficiency.

In the ultrasonic wave cosmetic device in the fourth aspect of the present invention, the drive unit produces one of the third harmonic frequency as the drive frequency. According to this structure, since one of the third harmonic frequencies is used as the drive frequency, the structure of the drive unit is simplified, thereby achieving small size and low cost.

In the ultrasonic wave cosmetic device in the fifth aspect of the present invention, the drive unit includes a separately excited oscillator for determining the drive frequency. According to this structure, since the separately excited oscillator is used, the oscillation frequency (drive frequency) becomes adjustable. Due to this, the desired characteristics can be achieved by the adjustment during the production of the ultrasonic wave vibration element and the horn even when the characteristics thereof vary.

In the ultrasonic wave cosmetic device in the sixth aspect of the present invention, the drive unit includes a self-excited oscillator for determining the drive frequency. According to this structure, since the self-excited oscillator is used, the drive unit with improved drive efficiency can be achieved.

In the ultrasonic wave cosmetic device in the seventh aspect of the present invention, the drive unit produces a plurality of frequencies of the second fundamental frequency and the third harmonic frequency as the drive frequencies, and has a frequency controller for switching between the plurality of drive frequencies. According to this structure, since a plurality of frequencies of the second fundamental frequency and the third harmonic frequency can be used as the drive frequencies and the frequency selector is provided to switch the drive frequencies, driving the vibration unit with plural frequencies can be easily done.

In the ultrasonic wave cosmetic device in the eight aspect of the present invention, the drive unit includes a separately excited oscillator for determining the drive frequency. According to this structure, since the separately excited oscillator is used, the oscillation frequency (drive frequency) becomes adjustable. Due to this, the desired characteristics can be achieved by the adjustment during the production of the ultrasonic wave vibration element and the horn even when the characteristics thereof vary.

In the ultrasonic wave cosmetic device in the ninth aspect of the present invention, the drive unit includes a self-induced oscillator for determining the drive frequency. According to this structure, since the self-excited oscillator is used, the drive unit with improved drive efficiency can be achieved.

In the ultrasonic wave cosmetic device in the tenth aspect of the present invention, the drive unit includes a power controller for controlling a drive power of each of the plurality of drive frequencies. According to this structure, since the power selector is provided, the output of the ultrasonic wave can be adjusted for each drive frequency. Further, since the transient stress applied to the joint surface between the ultrasonic wave vibration element and the horn generated right after switching the drive frequency can be reduced by decreasing the drive power during the switching, the effect of the stress (e.g., breakage of the joint surface) can be reduced.

In the ultrasonic wave cosmetic device in the eleventh aspect of the present invention, the drive unit includes a condition selector for selecting a switching order of the plurality of drive frequencies and a drive time of each of the drive frequencies. The frequency controller switches the drive frequencies under control of the condition selector. According to this structure, since the switching order of the drive frequencies and the drive time for each of the drive frequencies are selected, and the drive frequencies are switched under the control of the condition selector, the plurality of drive frequencies can be used under desired conditions.

In the ultrasonic wave cosmetic device in the twelfth aspect of the present invention, the drive unit includes a time selector for selecting a stop time during which a drive power of the drive frequency is stopped when the drive frequencies are switched. The frequency controller switches the drive frequencies under the control of the condition selector and the time selector. According to this structure, since the time selector selects the stop time during which the drive power of the drive frequency is stopped when the drive frequencies are switched and the frequency controller switches the drive frequencies based on the conditions received from the time selector, the transient stress applied to the joint surface between the ultrasonic wave vibration element and the horn generated right after the drive frequency switch can be reduced. Due to this, it is possible to reduce the effects of the stress (e.g. breakage of the joint surface) and also to prevent the surface of the horn from heating.

In the ultrasonic wave cosmetic device in the thirteenth aspect of the present invention, the drive unit includes a frequency mixer for mixing a plurality of drive frequencies selected from the second fundamental frequency and the third harmonic frequency and for producing a frequency mixed wave which is used as the drive frequency. According to this structure, since the mixed frequency wave is generated by mixing the second fundamental frequency and the third harmonic frequency by the frequency mixer and the drive unit drives the vibration unit by the mixed frequency wave, the effects based on the plurality of frequencies can be achieved at the same time.

In the ultrasonic wave cosmetic device in the fourteenth aspect of the present invention, the drive unit includes output power adjustment means for adjusting an output power of each of the drive frequencies. According to this structure, the output power of the ultrasonic wave can be adjusted for each of the drive frequencies.

In the ultrasonic wave cosmetic device in the fifteenth aspect of the present invention, the vibration unit is comprised of an ultrasonic wave vibration element and a horn. According to this structure, since the vibration unit is structured with one ultrasonic wave vibration element and one horn, it becomes simple and low cost.

In the ultrasonic wave cosmetic device in the sixteenth aspect of the present invention, the vibration unit is comprised of a plurality of ultrasonic wave vibration elements and a horn. According to the above structure, since the vibration unit is structured with several ultrasonic wave vibration elements and one horn, the number of frequencies proportional to the number of ultrasonic wave vibration elements can be used, and thus, various methods of use can be applied.

In the ultrasonic wave cosmetic device in the seventeenth aspect of the present invention, the drive unit drives each of the plurality of ultrasonic wave vibration elements separately. According to this structure, since the drive unit drives each of the several ultrasonic wave vibration elements, the number of frequencies proportional to the number of ultrasonic wave vibration elements can be used, and thus, various methods of use can be applied.

In the ultrasonic wave cosmetic device in the eighteenth aspect of the present invention, the drive unit drives the plurality of ultrasonic wave vibration elements at the same time. According to this structure, since the drive unit drives the several ultrasonic wave vibration elements at the same time, the effects based on the number of frequencies proportional to the number of ultrasonic wave vibration elements can be achieved at the same time.

In the ultrasonic wave cosmetic device in the nineteenth aspect of the present invention, the drive unit drives the plurality of ultrasonic wave vibration elements while sequentially switching them. According to this structure, since the drive unit sequentially switches and drives the several ultrasonic wave vibration elements, the number of frequencies proportional to the number of ultrasonic wave vibration elements can be used, and thus, various methods of use can be applied.

BRIEF DESCRIPTION OF THE DRAWINGS

FIGS. 11A–11D are waveform diagrams showing the operation of the ultrasonic wave cosmetic device in the tenth embodiment of the present invention.

FIGS. 19A and 19B are schematic block diagrams showing the structure of the ultrasonic wave cosmetic device in the fifteenth embodiment of the present invention.

DETAILED DESCRIPTION OF THE INVENTION

Figure 22A:
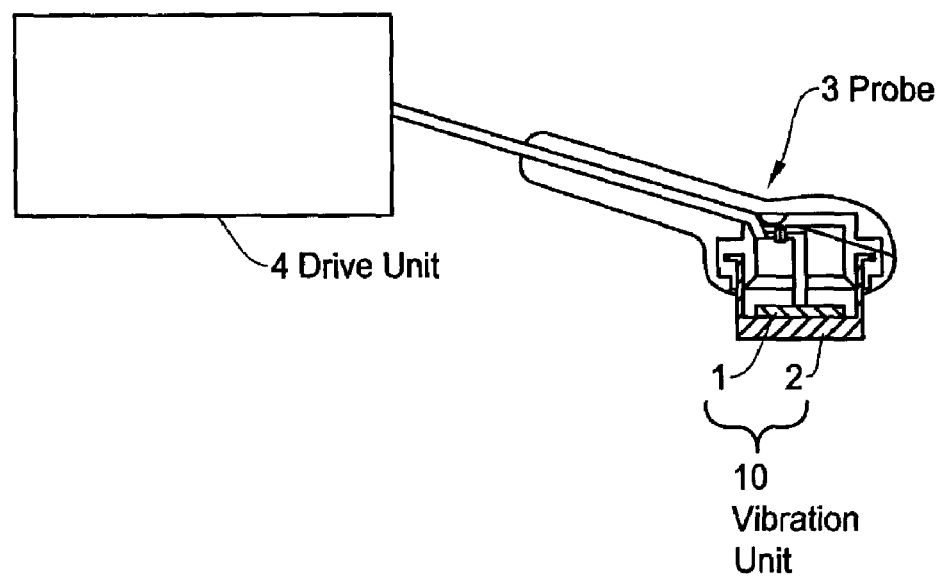
FIG. 22A is a schematic diagram and FIG. 22B is a cross sectional view respectively showing the structure of the conventional ultrasonic wave cosmetic device.
Figure 22B:
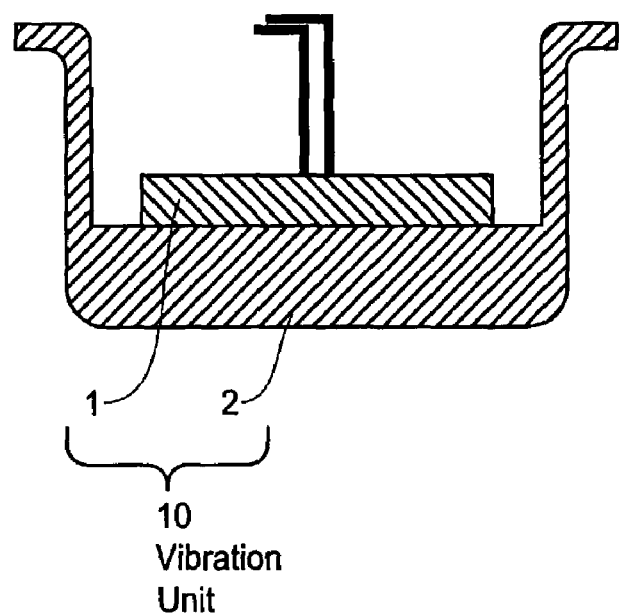

The structure of the ultrasonic wave cosmetic device related to the first embodiment of the present invention is the same as the conventional structure shown in FIG. 22, although a drive signal (ultrasonic wave) is different. As shown in FIG. 22, the ultrasonic wave cosmetic device is comprised of an ultrasonic wave vibration element 1 with a thickness of TH1 for generating ultrasonic waves, a probe 3 having a vibration unit 10, and a drive unit 4 for driving the ultrasonic wave vibration element 1. The vibration unit 10 has one surface which comes in contact with the facial skin and another surface which is structured by a horn 2 with a thickness of TH2 connected to the ultrasonic wave vibration element 1. The drive unit 4 can be installed inside the probe 3. The ultrasonic wave vibration element 1 is made of, for example, piezoelectric ceramic, and the horn 2 is made of, for example, aluminum.

Figure 1:
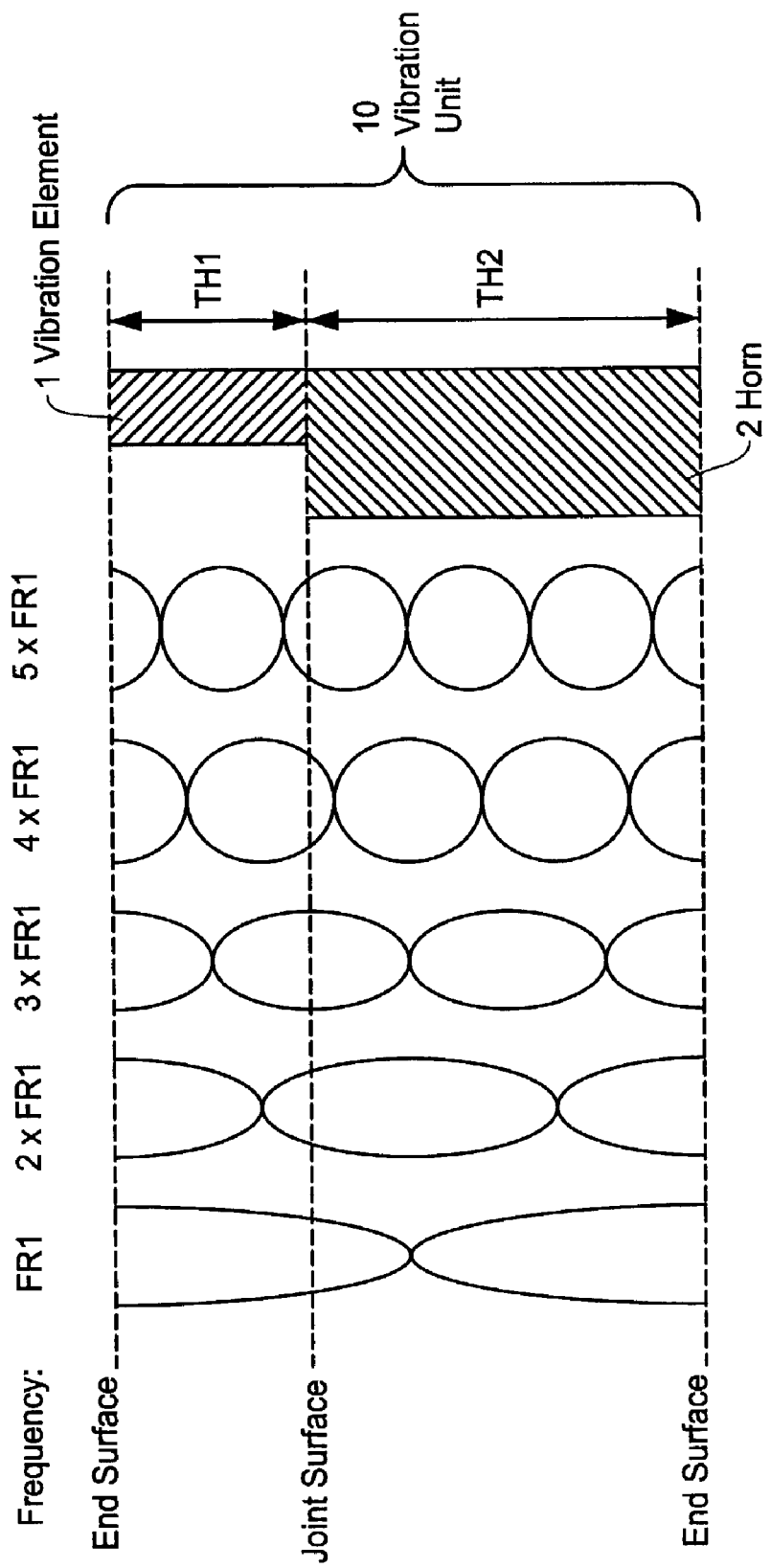
FIG. 1 is a diagram showing the condition of the ultrasonic wave (standing wave) propagating through the vibration unit of the ultrasonic wave cosmetic device in the first embodiment of the present invention.
Figure 23:
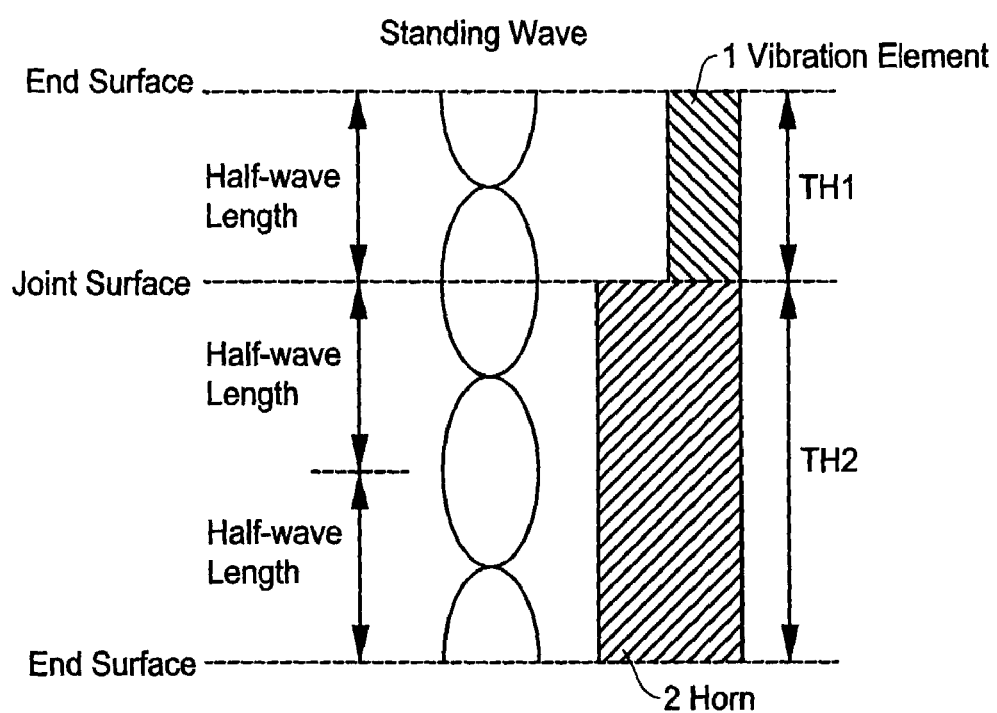
FIG. 23 is a diagram showing the condition of the ultrasonic wave (standing wave) propagating through the vibration unit in the conventional ultrasonic wave cosmetic device.

FIG. 1 is a diagram showing the condition of the ultrasonic waves (standing waves) propagating through the vibration unit 10 in the ultrasonic wave cosmetic device related to the first embodiment of the present invention. Similar to FIG. 23, for convenience of illustration, the longitudinal ultrasonic wave is shown as a transversal wave. Also, since the wavelength $\lambda$ of the ultrasonic wave propagating through a medium changes by the speed (sound velocity) of the ultrasonic wave (wavelength=sound velocity/frequency), a difference will arise in the wavelength of the ultrasonic wave propagating through the medium with a different velocity. However, for convenience of illustration, it is assumed that the wavelength $\lambda$ of the ultrasonic wave will not change by the medium.

In FIG. 1, a cross section of the vibration unit 10 is shown on the right side. The waveforms of the ultrasonic wave in the vibration unit 10 are shown in the order of drive frequency from the left toward the right. In this example, the drive frequencies are in the order of a first fundamental frequency FR1 where a half-wave length $\lambda/2$ of the ultrasonic wave propagating through the vibration unit 10 substantially matches the thickness of vibration unit 10 (TH1+

TH2), a second harmonic frequency which is twice the first fundamental frequency (2×FR1), a third harmonic frequency which is three times the first fundamental frequency (3×FR1), a fourth harmonic frequency which is four times the first fundamental frequency (4×FR1), and a fifth harmonic frequency five times the first fundamental frequency (5×FR1) from the left to right.

More specifically, when the thickness TH1 of the ultrasonic wave vibration element 1 and the thickness TH2 of the horn 2 are both 1.5 mm, the first fundamental frequency FR1 will be 0.8 MHz, the second harmonic frequency will be 1.6 MHz, the third harmonic frequency will be 2.4 MHz, the fourth harmonic frequency will be 3.2 MHz, and the fifth harmonic frequency will be 4.0 MHz, respectively. Consequently, in this invention, it has become possible to drive the vibration element 1 at a high frequency (4.0 MHz) as well as with a plurality of frequencies (5 different frequencies in this case).

Figure 2:
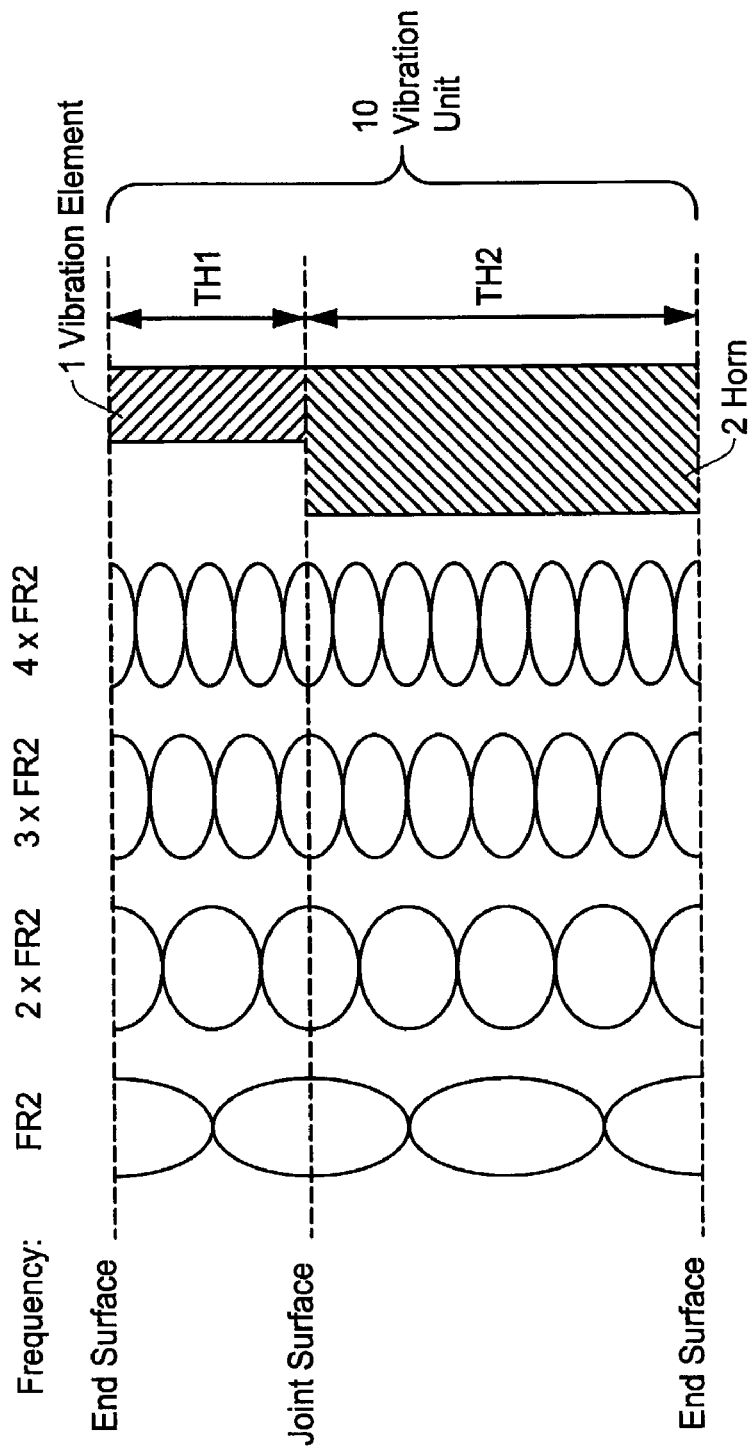
FIG. 2 a diagram showing the condition of the ultrasonic wave (standing wave) propagating through the vibration unit of the ultrasonic wave cosmetic device in the second embodiment of the present invention.

The structure of the ultrasonic wave cosmetic device related to the second embodiment of the present invention has the same structure as in the first embodiment, although a drive signal (ultrasonic wave) is different. FIG. 2 is a diagram showing the condition of the ultrasonic wave (standing wave) propagating through the vibration unit 10 in the ultrasonic wave cosmetic device related to the second embodiment of the present invention. Similar to FIG. 1, for convenience of illustration, the longitudinal ultrasonic wave is shown as a transversal wave. Also, since the wavelength λ of the ultrasonic wave propagating through the medium changes by the speed (sound velocity) of the ultrasonic wave (wavelength=sound velocity/frequency), a difference will arise in the wavelength of the ultrasonic wave propagating through the medium with a different velocity. However, for convenience of illustration, it is assumed that the wavelength λ of the ultrasonic wave will not change by the medium.

In FIG. 2, a cross section of the vibration unit 10 is shown on the right side. The waveforms of the ultrasonic wave in the vibration unit 10 are shown in the order of drive frequency from the left toward the right. In this example, the drive frequencies are in the order of a second fundamental frequency FR2 where a half-wave length λ/2 of the ultrasonic wave propagating through the vibration unit 10 substantially matches the thickness TH1 of the vibration element 1, a second harmonic frequency which is twice the second fundamental frequency (2×FR2), a third harmonic frequency which is three times the second fundamental frequency (3×FR2), a fourth harmonic frequency which is four times the second fundamental frequency (4×FR2), and a fifth harmonic frequency five times the second fundamental frequency (5×FR2) from the left to right.

As shown in FIG. 2, the joint surface connecting the ultrasonic wave vibration element 1 and the horn 2 is aligned with the mid-points of the standing waves, making the stress caused by the vibrations at the joint surface almost zero (=0). According to this effect, there is substantially no loss in drive energy at the joint surface, thereby improving a drive efficiency as well as preventing damages such as breakage of the joint surface.

The structure of the ultrasonic wave cosmetic device related to the third embodiment of the present invention has the same structure as in the first embodiment. The condition of the ultrasonic waves (standing waves) propagating through the vibration unit 10 of the ultrasonic wave cosmetic device related to the third embodiment of the present invention is, for example, the waveforms of the ultrasonic waves of vibration unit 10 when the second fundamental frequency FR2 and third harmonic frequency which is three times the second fundamental frequency (3×FR2) of FIG. 2 are used as drive frequencies.

Since one of either the second fundamental frequency or the third harmonic frequency is used as the drive frequency, the displacement of the ultrasonic wave vibration element 1 between the surface facing the horn 2 and the other surface will be in the opposite directions. Due to this, the ultrasonic wave vibration element 1 mechanically resonates at the drive frequency, resulting in further improvement of the drive efficiency.

Figure 3:
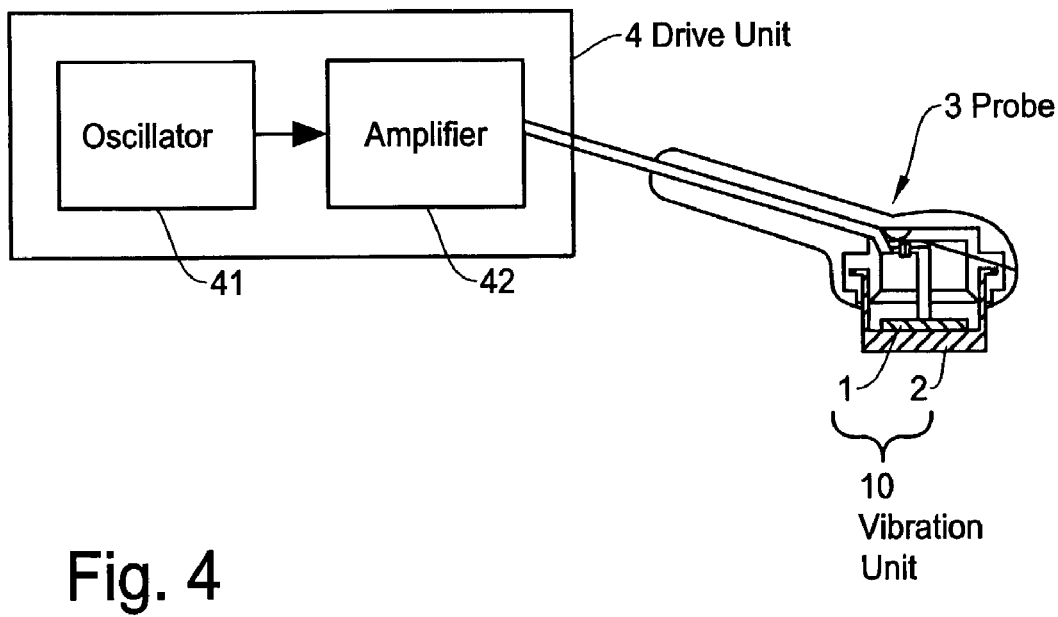
FIG. 3 is a schematic block diagram showing the structure of the ultrasonic wave cosmetic device in the fourth embodiment of the present invention.

FIG. 3 is a diagram showing the structure of the ultrasonic wave cosmetic device related to the fourth embodiment of the present invention. The probe 3 has the same structure as that in the first embodiment. The drive unit 4 is comprised of an oscillator 41 for determining the drive frequency and an amplifier 42 for amplifying the signal from the oscillator 41. In other words, the drive unit 4 drives the vibration unit 10 by a single drive frequency.

The condition of the ultrasonic waves (standing waves) propagating through the vibration unit 10 of the ultrasonic wave cosmetic device related to the fourth embodiment of the present invention is, for example, the waveforms of the ultrasonic waves of vibration unit 10 when only the third harmonic frequency (3×FR2) of FIG. 2 is used as the drive frequency. Since the drive unit 4 is to drive only one drive frequency, the structure of drive unit 4 is simplified, allowing the reduction in size and cost.

Figure 4:
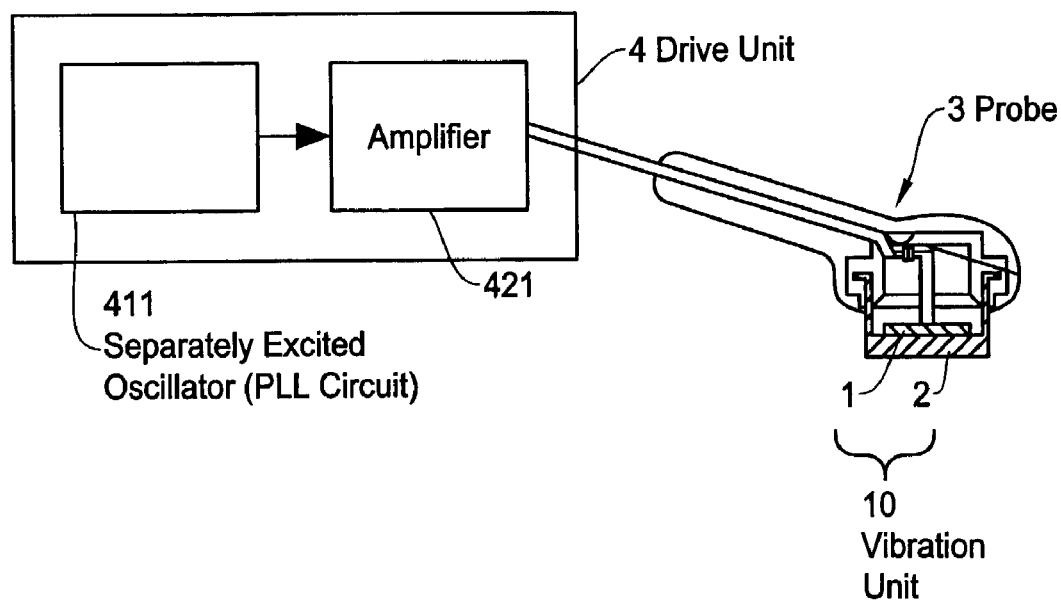
FIG. 4 is a schematic block diagram showing the structure of the ultrasonic wave cosmetic device in the fifth embodiment of the present invention.

FIG. 4 is a diagram showing the structure of the ultrasonic wave cosmetic device related to the fifth embodiment of the present invention. The probe 3 has the same structure as that in the first embodiment. The drive unit 4 is comprised of a separately excited oscillator 411 for determining the drive frequency and an amplifier 421 for amplifying the signal from the separately excited oscillator 411. In other words, drive element 4 drives the vibration unit 10 by a single drive frequency.

The separately excited oscillator 411 is structured with, for example, a PLL (phase-locked loop) circuit. The PLL circuit is a well known structure provided with, for example, a programmable frequency divider, a phase comparator, a VCO (voltage controlled oscillator), and a low-pass filter. A voltage supplied from the phase comparator is converted into a DC signal by the low-pass filter and is applied to the VCO to adjust the oscillation frequency.

Since the drive unit 4 is comprised of the separately excited oscillator 411, the oscillation frequency (drive frequency) is adjustable. Thus, during the production of ultrasonic wave vibration element 1 and the horn 2, the desired characteristics can be achieved by such adjustments even when their characteristics vary.

Figure 5:
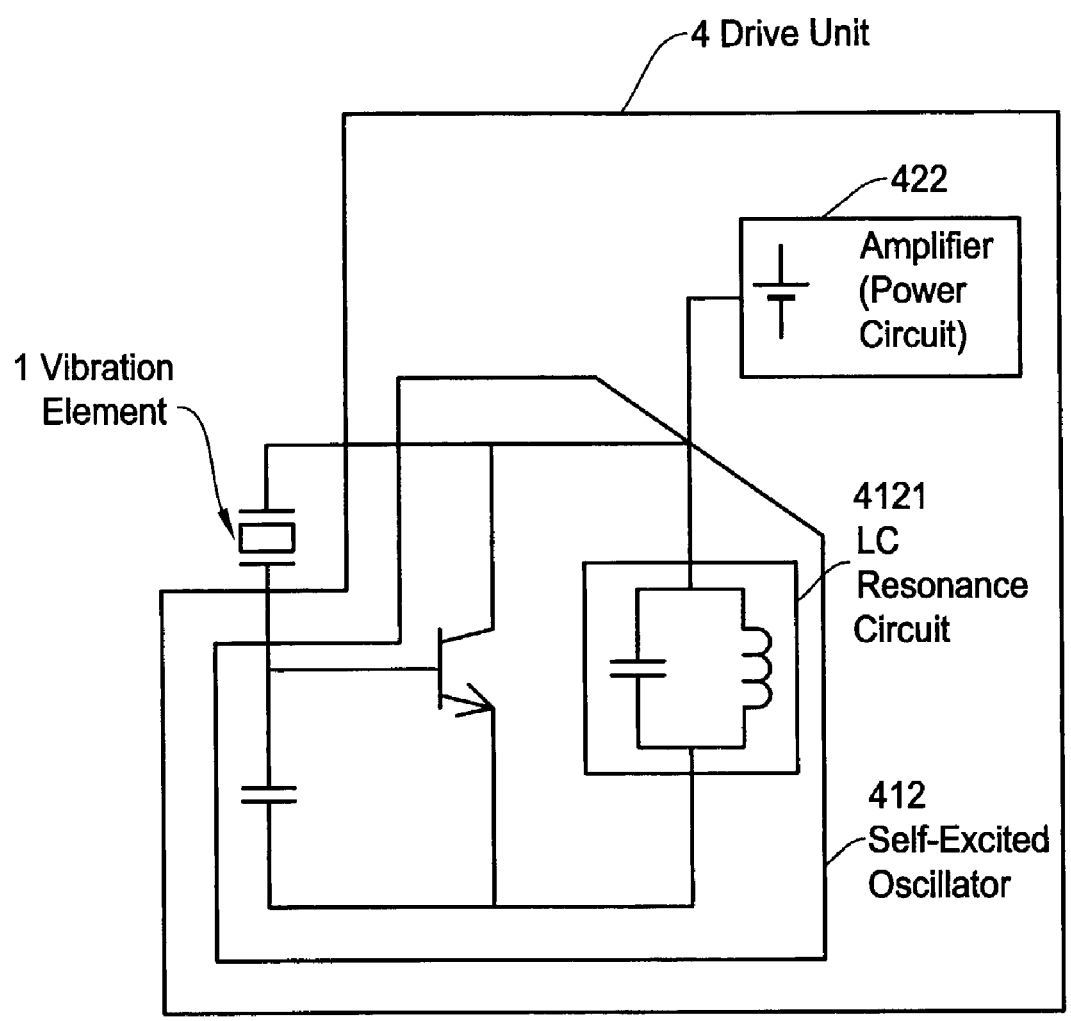
FIG. 5 is a block diagram showing the structure of the ultrasonic wave cosmetic device related in the sixth embodiment of the present invention.

FIG. 5 is a diagram showing the structure of the ultrasonic wave cosmetic device related to the sixth embodiment of the present invention. The probe (not shown in FIG. 5) has the same structure as that shown in FIGS. 3 and 4. The drive unit is comprised of a self-excited oscillator 412 for determining the drive frequency and an amplifier 422 for amplifying the signal from the self-excited oscillator 412. In other words, drive element 4 drives the vibration unit 10 by a single drive frequency.

The self-excited oscillator 412 is structured with, for example, a Colpitts oscillation circuit. As known in the art, a Colpitts oscillation circuit is provided with an LC resonance circuit 4121 as a feedback circuit. Since the drive unit 4 has the self-excited oscillator 412, which is able to determine its oscillation frequency, the drive unit 4 is able to achieve a high drive efficiency.

Figure 6:
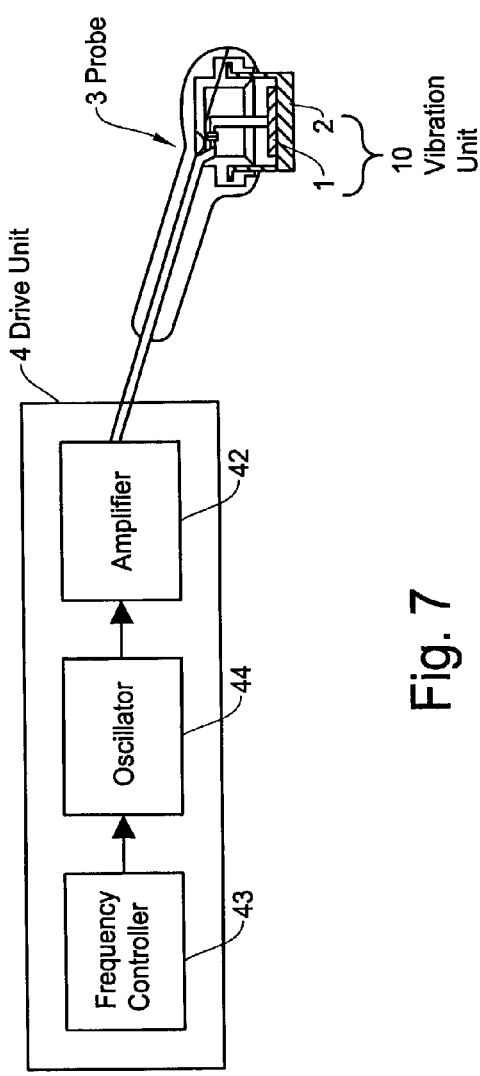
FIG. 6 is schematic block diagram showing the structure of the ultrasonic wave cosmetic device in the seventh embodiment of the present invention.

FIG. 6 is a block diagram showing the structure of the ultrasonic wave cosmetic device related to the seventh embodiment of the present invention. The probe 3 has the same structure as that, in the first embodiment. The drive unit 4 is comprised of an oscillator 44 for determining the drive frequency, an amplifier 42 for amplifying the drive signal from the oscillator 44, and a frequency controller 43 for controlling the drive frequency from the oscillator 44. Since the drive unit 4 includes the frequency controller 43, it can easily drive the vibration unit 10 with several different frequencies.

The frequency controller 43 changes the drive frequency upon receiving the instruction by a user of the ultrasonic wave cosmetic device. Alternatively, by setting the change conditions such as an switching order of several frequencies and each drive time length in advance, the frequency controller 43 changes the drive frequency based on such conditions.

Figure 7:
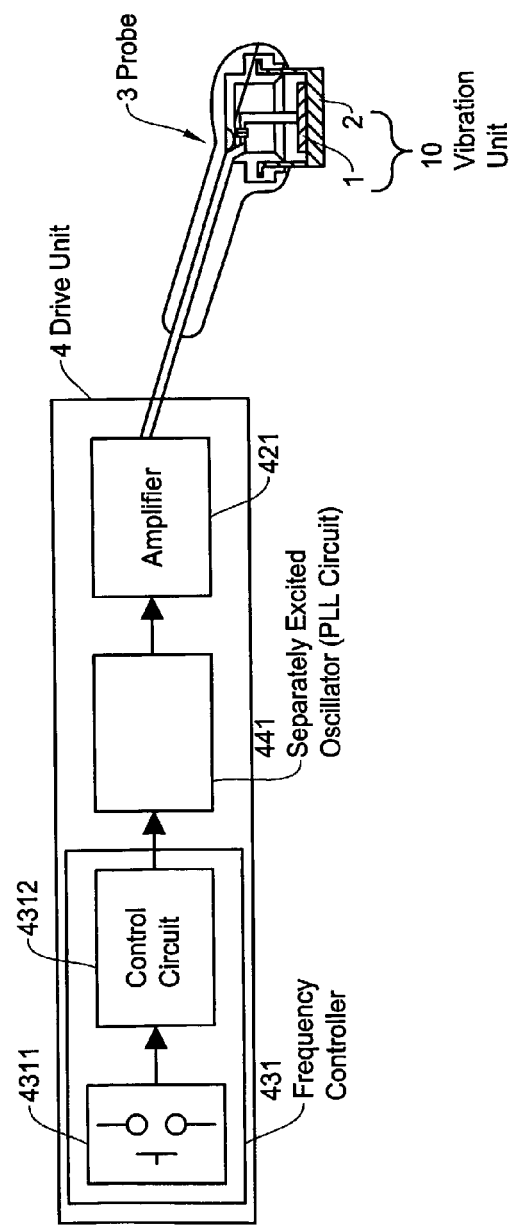
FIG. 7 is a schematic block diagram showing the structure of the ultrasonic wave cosmetic device in the eighth embodiment of the present invention.

FIG. 7 is a block diagram showing the structure of the ultrasonic wave cosmetic device related to the eighth embodiment of the present invention. The probe 3 has the same structure as that in the first embodiment. The drive unit 4 is comprised of a separately excited oscillator 441 for determining the drive frequency, an amplifier 421 for amplifying the signals from the separately excited oscillator 441, and a frequency controller 431 for controlling the drive frequency from the separately excited oscillator 441.

The separately excited oscillator 441, similar to the fourth embodiment, is structured with, for example, a PLL circuit. The frequency controller 431 is comprised of a switch 4311 for producing a frequency switch signal upon the operation by the user of the ultrasonic wave cosmetic device, and a control circuit 4312 for changing the oscillation frequency of the separately excited oscillator 441 based on the switch signal from the switch 4311.

Figure 8:
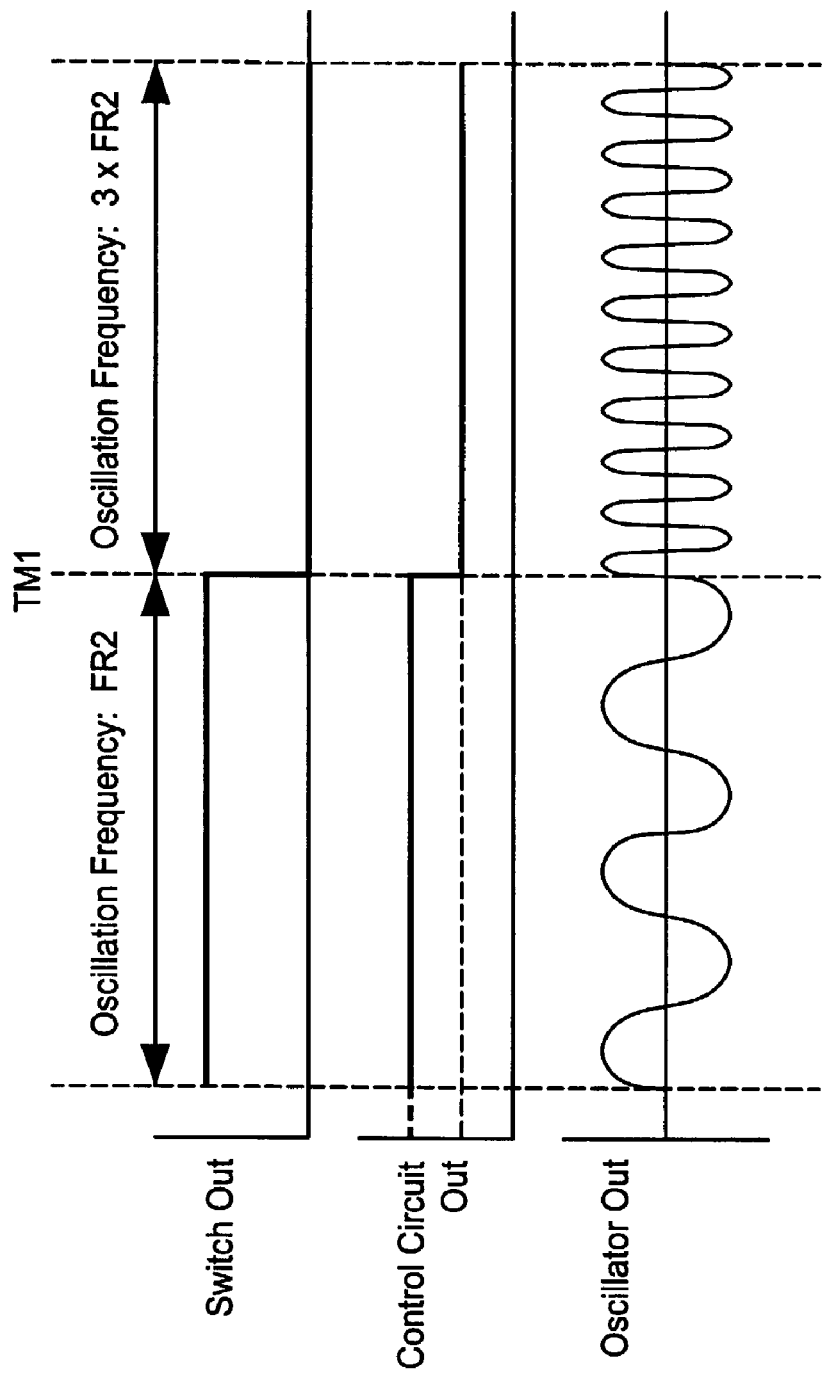
FIGS. 8A–8C are waveform diagrams showing the operation of the ultrasonic wave cosmetic device in the eighth embodiment of the present invention.

FIGS. 8A–8C are waveform diagrams for explaining an operational procedure of the ultrasonic wave cosmetic device related to the eighth embodiment of the present invention. In the diagrams, the horizontal axis represents time, and the vertical axis represents a signal level at an output of the switch 4311 in FIG. 8A, a signal level at an output of the control circuit 4312 in FIG. 8B, and a signal level of an output of the separately excited oscillator 441 in FIG. 8C. Here, the operation is explained for the case where the second fundamental frequency FR2 and the third harmonic frequency which is three times the second fundamental frequency (3×FR2) as shown in FIG. 2 are switched with each other as the drive frequency.

As an initial condition, the second fundamental frequency FR2 is selected. First, at time TM1, the output of the switch 4311 is changed from the second fundamental frequency FR2 to the third harmonic frequency (3×FR2) upon receiving the instruction by the user of the ultrasonic wave cosmetic device. Based on this change, a control signal is supplied from the control circuit 4312 to the oscillator 441. Based on the control signal, the drive frequency from the separately excited oscillator 441 is switched from the second fundamental frequency FR2 to the third harmonic frequency (3×FR2).

Since the drive unit 4 includes the frequency controller 431, the drive frequency can be switched in response to the operation by the user of the ultrasonic wave cosmetic device. Further, since the drive unit 4 includes the separately excited oscillator 441, it is possible to adjust the oscillation frequency (drive frequency). Thus, during the production of the ultrasonic wave vibration element 1 and the horn 2, the desired characteristics can be achieved by this frequency adjustment even when the characteristics of these components vary.

Figure 9:
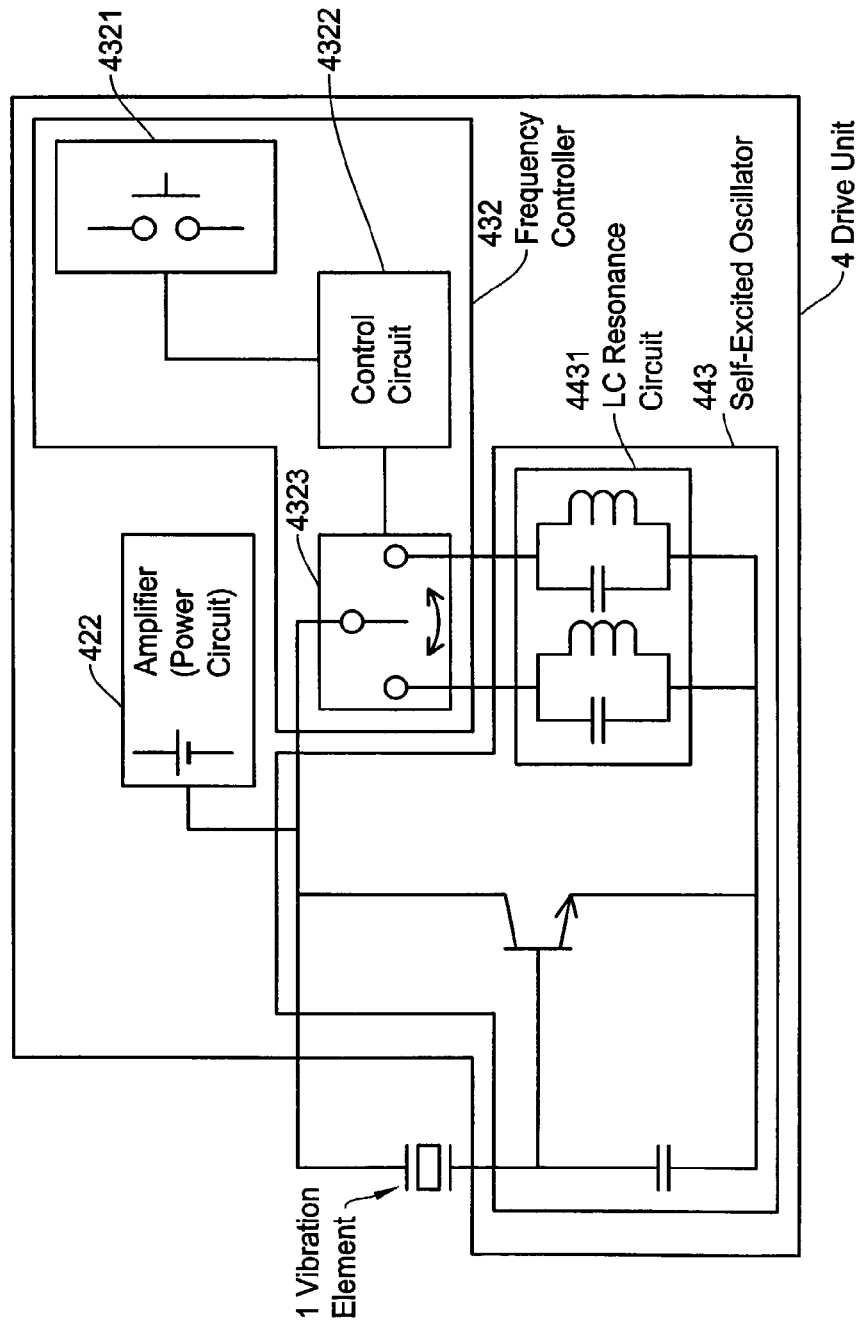
FIG. 9 is a block diagram showing the structure of the ultrasonic wave cosmetic device in the ninth embodiment of the present invention.

FIG. 9 is a diagram showing the structure of the ultrasonic wave cosmetic device related to the ninth embodiment of the present invention. The probe 3 has the same structure as that in the first embodiment. The drive unit 4 is comprised of a self-excited oscillator 443 for determining the drive frequency, an amplifier 422 for amplifying the drive signal from the self-excited oscillator 443, and a frequency controller 432 for controlling the drive frequency from the self-excited oscillator 443. The self-excited oscillator 443 is comprised of an LC resonance circuit 4431, which is capable of generating two different resonance frequencies (such as the second fundamental frequency FR2 and the third harmonic frequency (3×FR2) in FIG. 2).

The frequency controller 432 is comprised of a switch 4321 for producing a frequency switch signal upon the operation by the user of the ultrasonic wave cosmetic device, an internal switch 4323 for switching the LC resonance circuit 4431 of the self-excited oscillator 443, and a control circuit 4322 for providing a control signal based to the internal switch 4323 based on the frequency switch signal from the switch 4321.

Based on the switch 4321, when receiving the operation by the user of the ultrasonic wave cosmetic device, the frequency switch signal is generated. Based on this frequency switch signal, a control signal is generated by the control circuit 4322. Further, based on this control signal, the LC resonance circuit 4431 of the self-excited oscillator 443 is switched by the internal switch 4323, thereby changing the drive frequency.

Since the drive unit 4 is comprised of the frequency controller 432, the drive frequency can be switched in response to the operation by the user of the ultrasonic wave cosmetic device. Further, since the drive unit 4 is also comprised of the self-excited oscillator 443, the drive unit 4 with a high drive efficiency can be achieved.

Figure 10A:
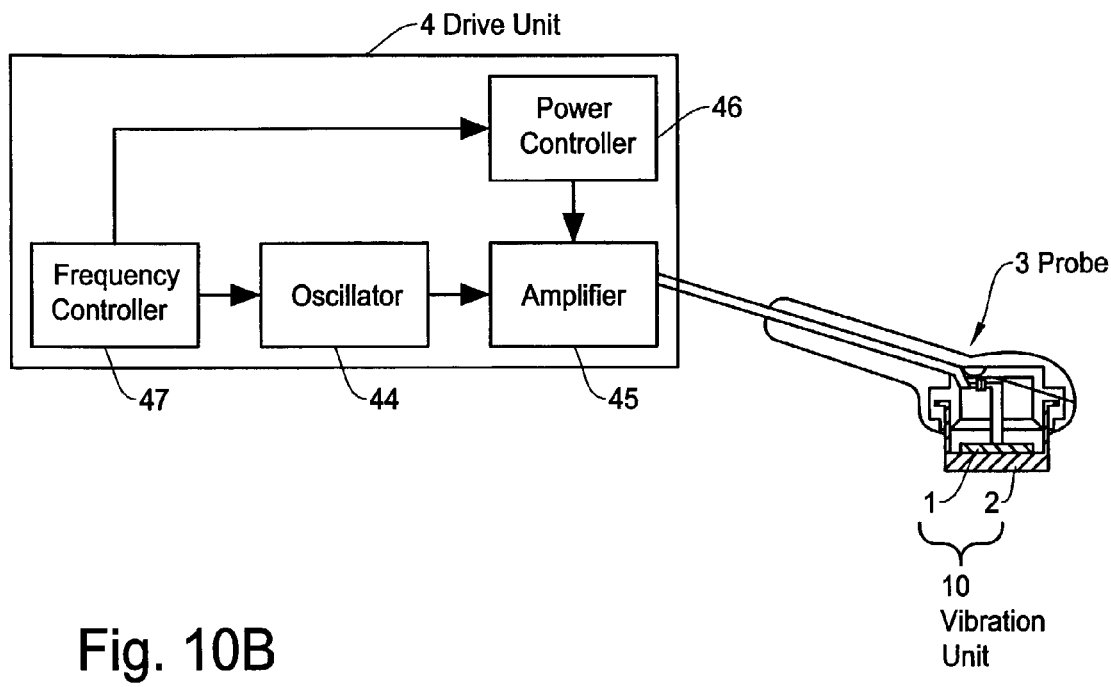
FIGS. 10A–10C are schematic block diagrams showing the structure of the ultrasonic wave cosmetic device in the tenth embodiment of the present invention.

FIG. 10A is a diagram showing the structure of the ultrasonic wave cosmetic device related to the tenth embodiment of the present invention. The probe 3 has the same structure as that in the first embodiment. The drive unit 4 is comprised of an oscillator 44 for determining the drive frequency, an amplifier 45 for amplifying the drive signal from the oscillator 44, a frequency controller 47 for controlling the drive frequency from the oscillator 44, and a power controller 46 for setting a drive power level for each drive frequency. The frequency controller 47 also supplies a control signal to the power controller 46.

Figure 10B:
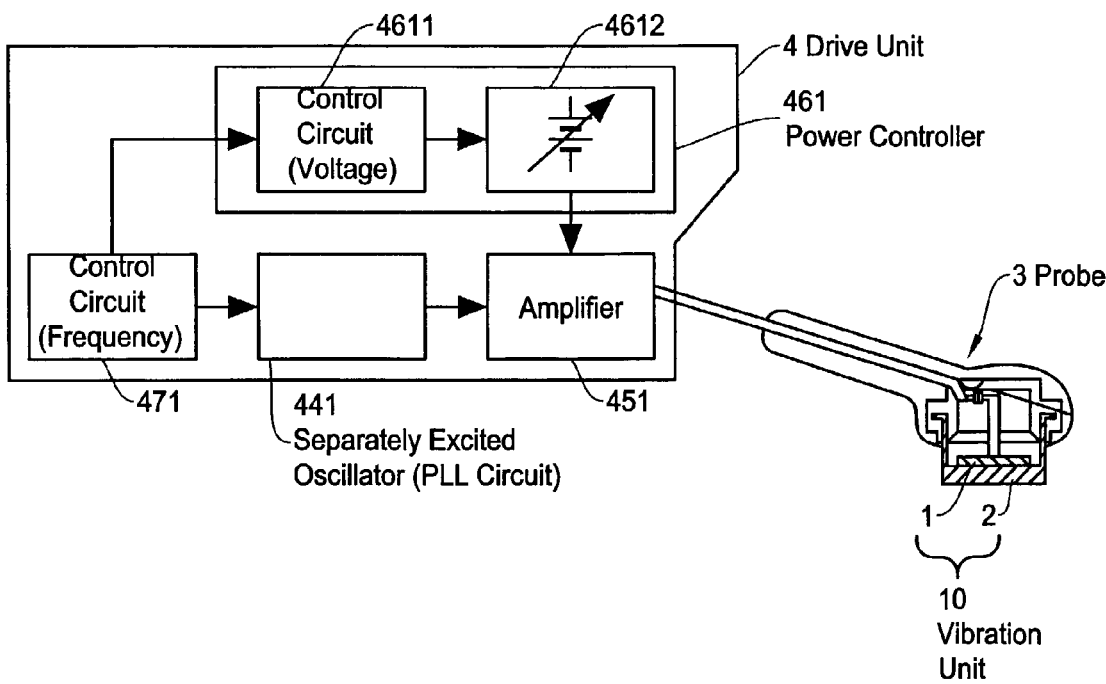
Figure 10C:
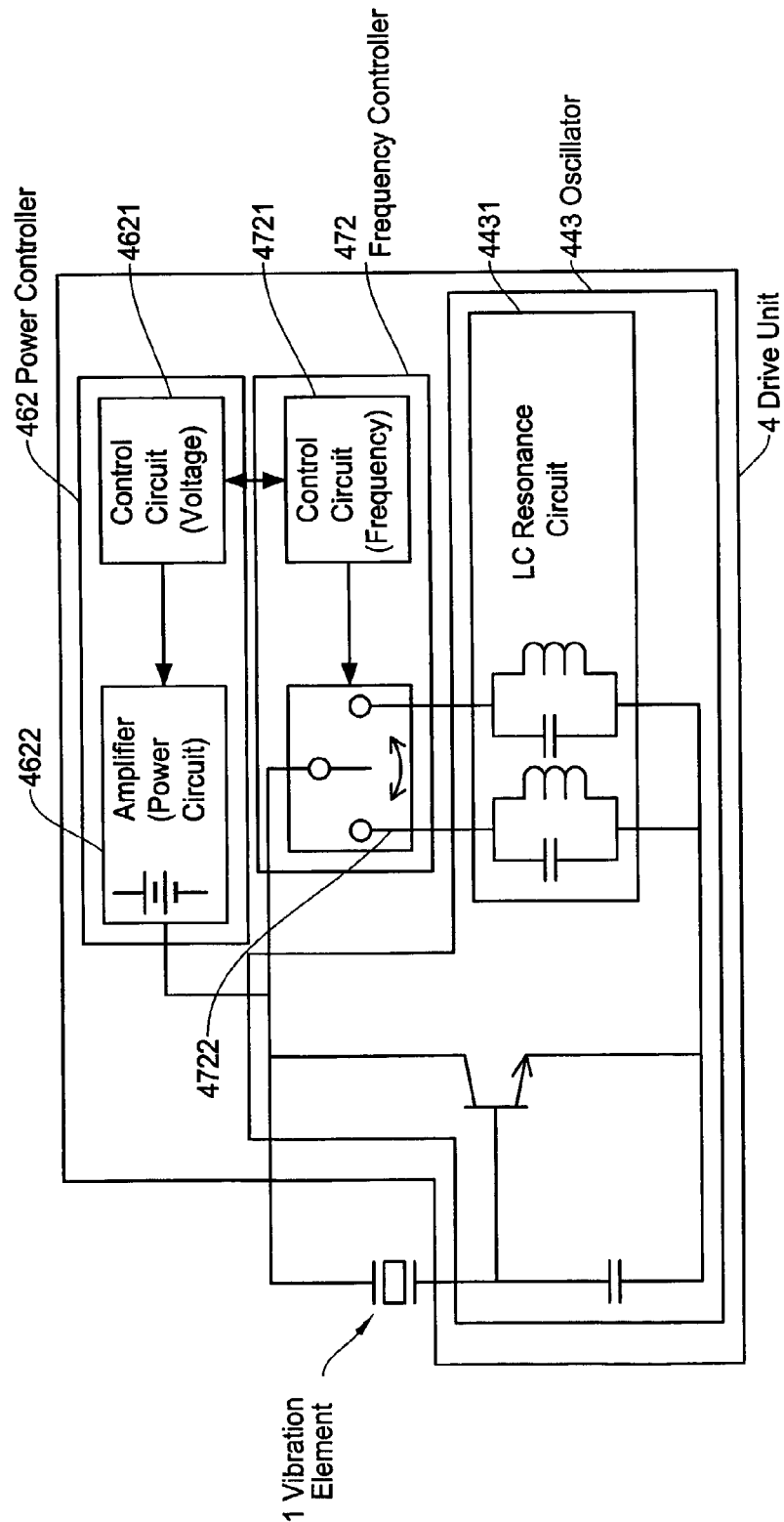

The power controller 46 sets the drive power level per every drive frequency based on the control information (information relating to the change in the drive frequency) from the frequency controller 47. FIG. 10B shows an example of the ultrasonic wave cosmetic device related to the tenth embodiment of the present invention when the oscillator is a separately excited oscillator. The drive unit 4 in FIG. 10B is comprised of a separately excited oscillator 441, an amplifier 451, a power controller 461 and a frequency control circuit 471. The power controller 461 includes a voltage control circuit 4611 and a power circuit 4612. FIG. 10C shows an example of the ultrasonic wave cosmetic device related to the tenth embodiment of the present invention when the oscillator is a self-excited oscillator. The drive unit 4 in FIG. 10C is comprised of an oscillator 443 having an LC resonance circuit 4431, a frequency controller 472, and a power controller 462. The frequency controller 472 includes an internal switch 4722 and a frequency control circuit 4721. The power controller 462 includes a voltage control circuit 4621 and a power circuit 4622.

FIGS. 11A–11D are waveform diagrams for explaining the operational procedure of the ultrasonic wave cosmetic device related to the tenth embodiment of the present invention. In the diagrams, the horizontal axis represents time, and the vertical axis represents an output of the frequency controller 47 in FIG. 11A, an output of the power controller 46 in FIG. 11B, an output of the oscillator 44 in FIG. 11C, and an output of the amplifier 45 in FIG. 11D. Here, the operation is explained for the case where the second fundamental frequency FR2 and the third harmonic frequency which is three times the second fundamental frequency (3×FR2) as shown in FIG. 2 are switched with each other as the drive frequency.

As an initial condition, the second fundamental frequency FR2 is selected. First, at time TM2, the output of the frequency controller 47 is changed from the second fundamental frequency FR2 to the third harmonic frequency (3×FR2) upon receiving the operation by the user of the ultrasonic wave cosmetic device. Based on this change, a control signal is supplied to the power controller 46. Based on this control signal, the drive frequency is switched from the second fundamental frequency FR2 to the third harmonic frequency (3×FR2) by the oscillator 44, and the drive power is changed by the amplifier 45.

Since drive unit 4 includes the power controller 46, the output of the ultrasonic wave of each drive frequency can be controlled. Further, by decreasing the drive power during switching the drive frequencies, transient stress at the joint surface between the ultrasonic wave vibration element 1 and the horn 2 produced right after the frequency switching can be reduced, thereby decreasing adverse effects (i.e., breakage of joint surface) of the stress.

Figure 12:
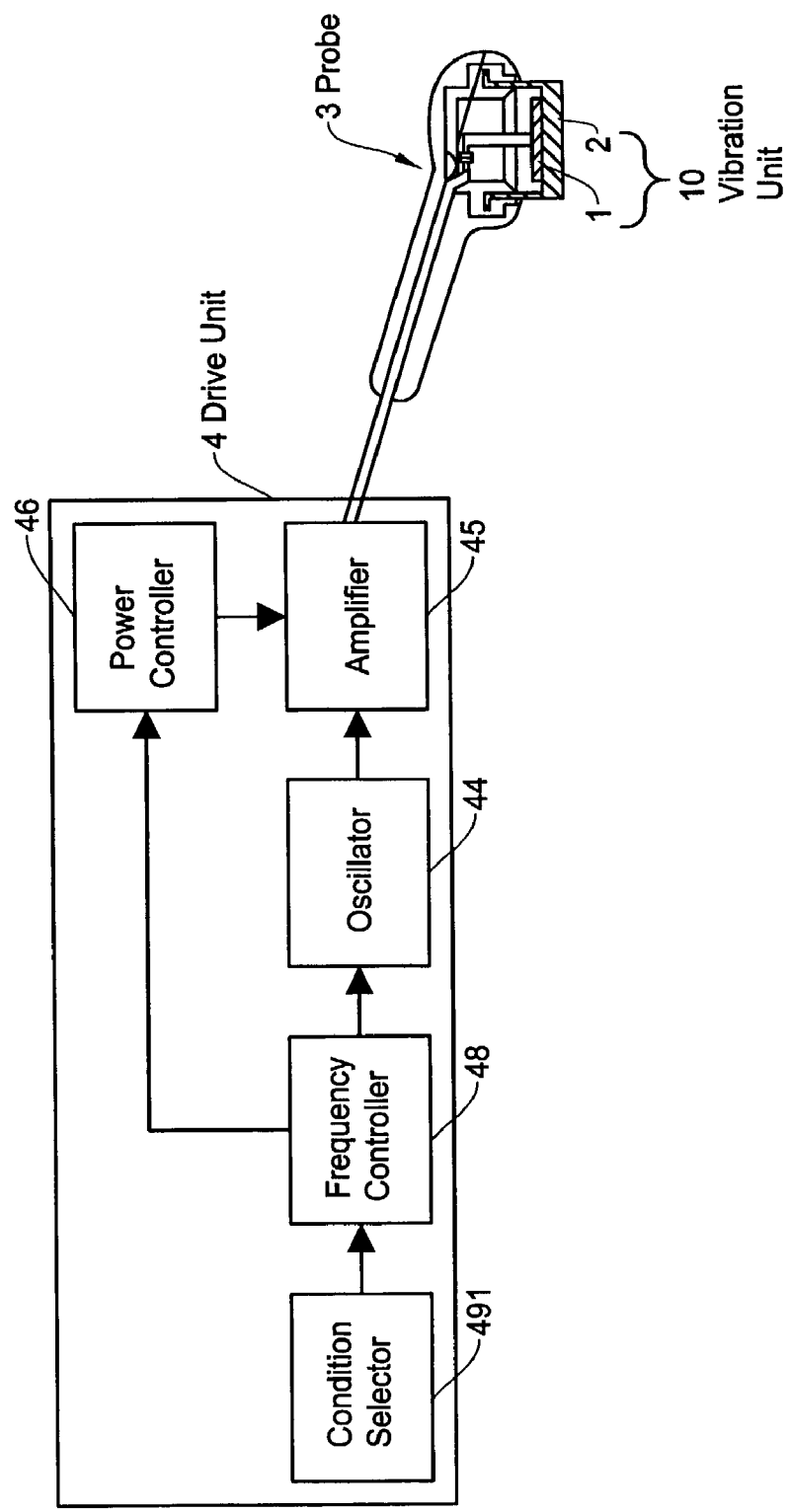
FIG. 12 is a schematic block diagram showing the structure of the ultrasonic wave cosmetic device in the eleventh embodiment of the present invention.

FIG. 12 is a diagram showing the structure of the ultrasonic wave cosmetic device related to the eleventh embodiment of the present invention. The structure of the probe 3 is the same as that in the first embodiment. The drive unit 4 is comprised of an oscillator 44 for determining the drive frequency, an amplifier 45 for amplifying the drive signal from the oscillator 44, a frequency controller 48 for controlling the frequency of the oscillator 44, a power controller 46 for controlling the drive power for each drive frequency, and a condition selector 491 for selecting the conditions to change the drive frequency. The frequency controller 48 also supplies a control signal to the power controller 46.

The condition selector 491 sets a switching order of the plurality of drive frequencies and a drive time per each of the drive frequencies. The frequency controller 48 changes the oscillation frequency of the oscillator 44 based on these conditions. Here, explanation will be made for the case where the change in the drive power of each drive frequency in the amplifier 45 is not conducted but only the drive frequency has to be changed.

Figure 13:
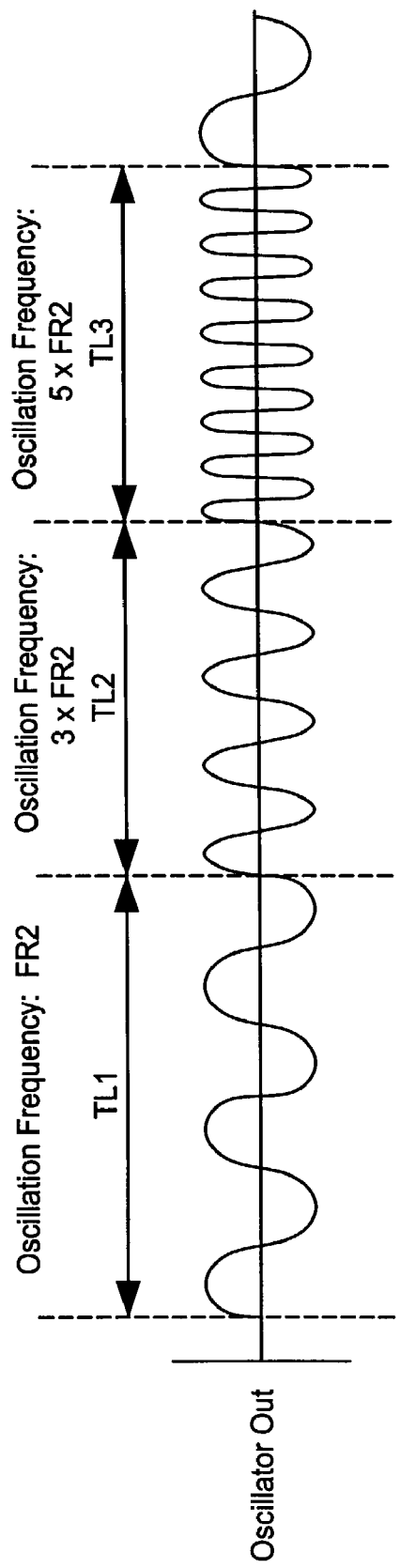
FIG. 13 is a waveform diagram showing the operation of the ultrasonic wave cosmetic device in the eleventh embodiment of the present invention.

FIG. 13 is a waveform diagram for explaining the operational procedure of the ultrasonic wave cosmetic device related to the eleventh embodiment of the present invention. In the diagram, the horizontal axis represents the time, and the vertical axis represents the output of the oscillator 44. Here, the case where the second fundamental frequency FR2 and the third harmonic frequency which is three times the second fundamental frequency (3×FR2) shown in FIG. 2, as well as the fifth harmonic frequency which is five times the second fundamental frequency (5×FR2) not shown in FIG. 2, are switched with one another as the drive frequencies will be explained.

It is assumed that by the condition selector 491, instructions, for example, by a user of the ultrasonic wave cosmetic device user is received. It is also assumed that the switching order of the drive frequencies is set in the order of second fundamental frequency, third harmonic frequency, and fifth harmonic frequency. The values of drive times TL1, TL2, and TL3 for the corresponding drive frequencies are also set.

First, by the condition selector 491, the switching order of the drive frequency and the drive time per drive frequency is supplied to the frequency controller 48. By the frequency controller 48, the drive frequencies from the oscillator 44 are changed based on this information. In other words, the second fundamental frequency FR2 is oscillated during the drive time TL1, the third harmonic frequency is oscillated during the drive time TL2, and the fifth harmonic frequency is oscillated during the drive time TL3. The above procedure is repeated thereafter.

Since the drive unit 4 includes the condition selector 491 and switches the drive frequencies by the frequency controller 48 under the conditions specified in the condition selector 491, the plurality of drive frequencies can be used under desired conditions.

Figure 14:
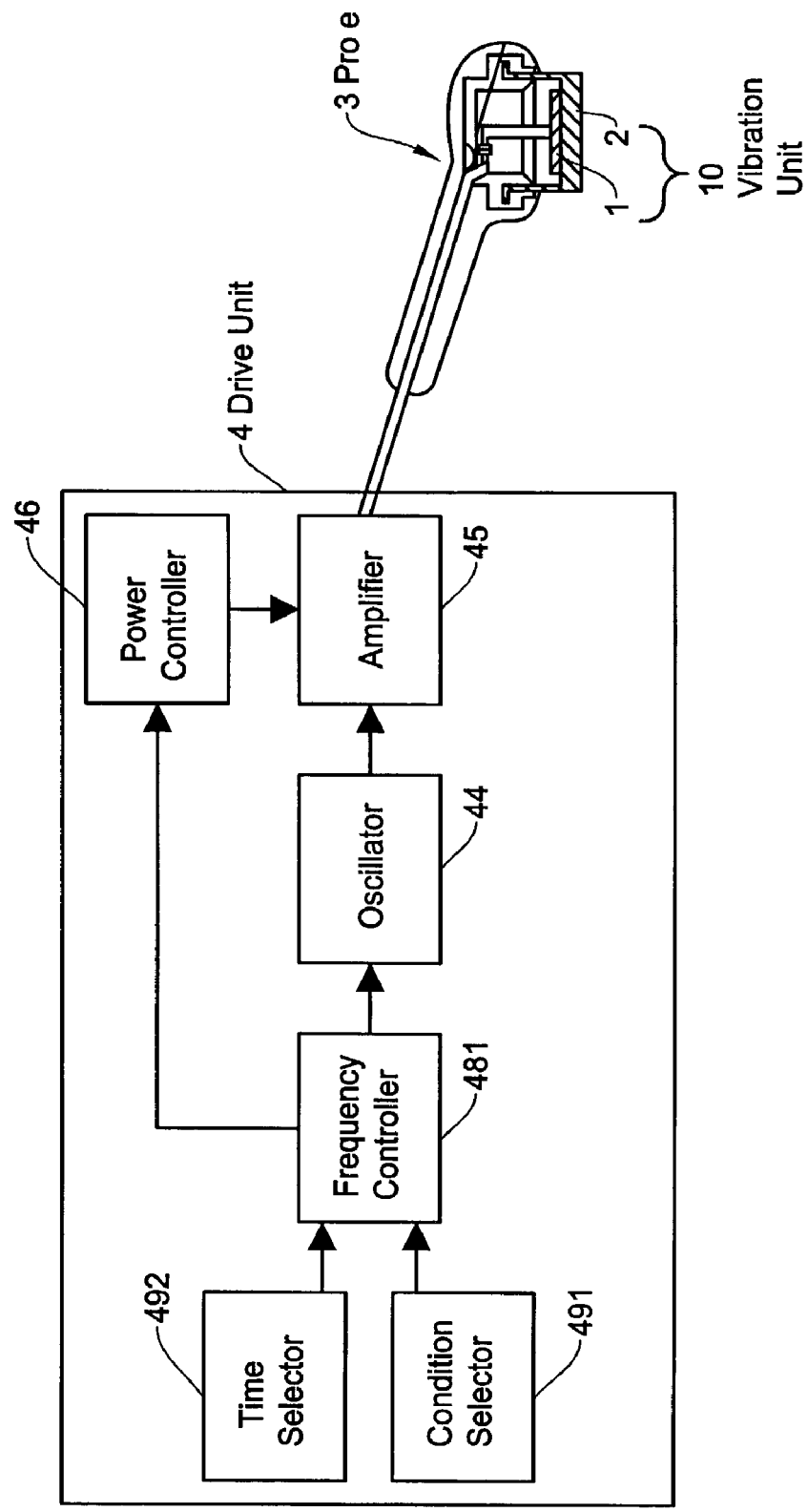
FIG. 14 is a block diagram showing the structure of the ultrasonic wave cosmetic device in the twelfth embodiment of the present invention.

FIG. 14 is a diagram showing the structure of the ultrasonic wave cosmetic device related to the twelfth embodiment of the present invention. The structure of the probe 3 is the same as that in the first embodiment. The drive unit 4 is comprised of an oscillator 44 for determining the drive frequency, an amplifier 45 for amplifying the drive signal from the oscillator 44, a frequency controller 481 for controlling the drive frequency from the oscillator 44, a power controller 46 for controlling the drive power for each drive frequency, a condition selector 491 for selecting the conditions for changing the drive frequency, and a time selector 492 for selecting a time to stop the drive power. The frequency controller 481 also supplies a control signal to the power controller 46.

The condition selector 491 sets and selects a switching order of a plurality of drive frequencies and a drive time for each drive frequency. The time selector 492 sets and selects the time to stop the drive power during the switching between the drive frequencies. The frequency controller 481 controls the drive frequency from the oscillator 44 based on the conditions set in the condition selector 491 and the time selector 492. Here, explanation will be made for the case where the drive power per drive frequency by the amplifier 45 is not changed but only the drive frequency is changed.

Figure 15:
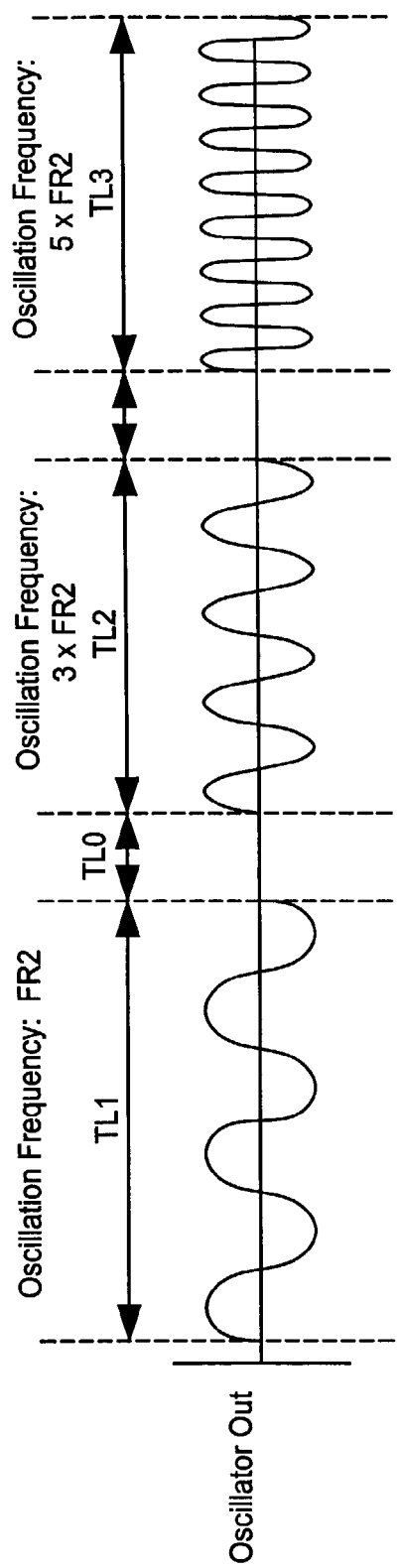
FIG. 15 is a waveform diagram showing the operation of the ultrasonic wave cosmetic device in the twelfth embodiment of the present invention.

FIG. 15 is a waveform diagram for explaining the operational procedure of the ultrasonic wave cosmetic device related to the twelfth embodiment of the present invention. In the diagram, the horizontal axis represents the time, and the vertical axis indicates the output of oscillator 44. Here, the case where the second fundamental frequency FR2 and the third harmonic frequency which is three times the second fundamental frequency (3×FR2) shown in FIG. 2, as well as the fifth harmonic frequency which is five times the second fundamental frequency (5×FR2) not shown in FIG. 2, are switched with one another as the drive frequencies will be explained.

It is assumed that by the condition selector 491, instructions by, for example, a user of the ultrasonic wave cosmetic device user is received and that the switching order of the drive frequencies is set in the order of second fundamental frequency, third harmonic frequency, and fifth harmonic frequency. It is also assumed that the values of drive times TL1, TL2, and TL3 for the corresponding drive frequencies are set. Further, by the time selector 492, a stop time TL0 is pre-set in memory means.

First, the switching order of the drive frequency and the drive time for each drive frequency is supplied to the frequency controller 481 by the condition selector 491. The stop time TL0 is supplied by the time selector 492, and based on this information, the drive frequency from the oscillator 44 is changed by the frequency controller 481. In other words, the oscillator 44 is oscillated at the second fundamental frequency FR2 during the drive time TL1, then stopped during the stop time TL0. Then, the oscillator 44 is oscillated at the third harmonic frequency (3×FR2) during the drive time TL2, then stopped during the stop time TL0. Further, the oscillator 44 is oscillated at the fifth harmonic frequency (5×FR2) during the drive time TL3, then stopped during the stop time TL0. The above procedure is repeated thereafter.

Since the drive unit 4 includes the time selector 492 for setting the time for stopping the drive power and switches the drive frequency by the frequency controller during the stop time conditions set in the time selector 492, the transient stress acted on the joint surface between the ultrasonic wave vibration element 1 and the horn 2 immediately after the drive frequencies are switched can be reduced. Hence, the effects of the stress (e.g., the breakage of the joint surface) can be reduced and heat generation on the surface of the horn 2 can also be prevented.

Figure 16:
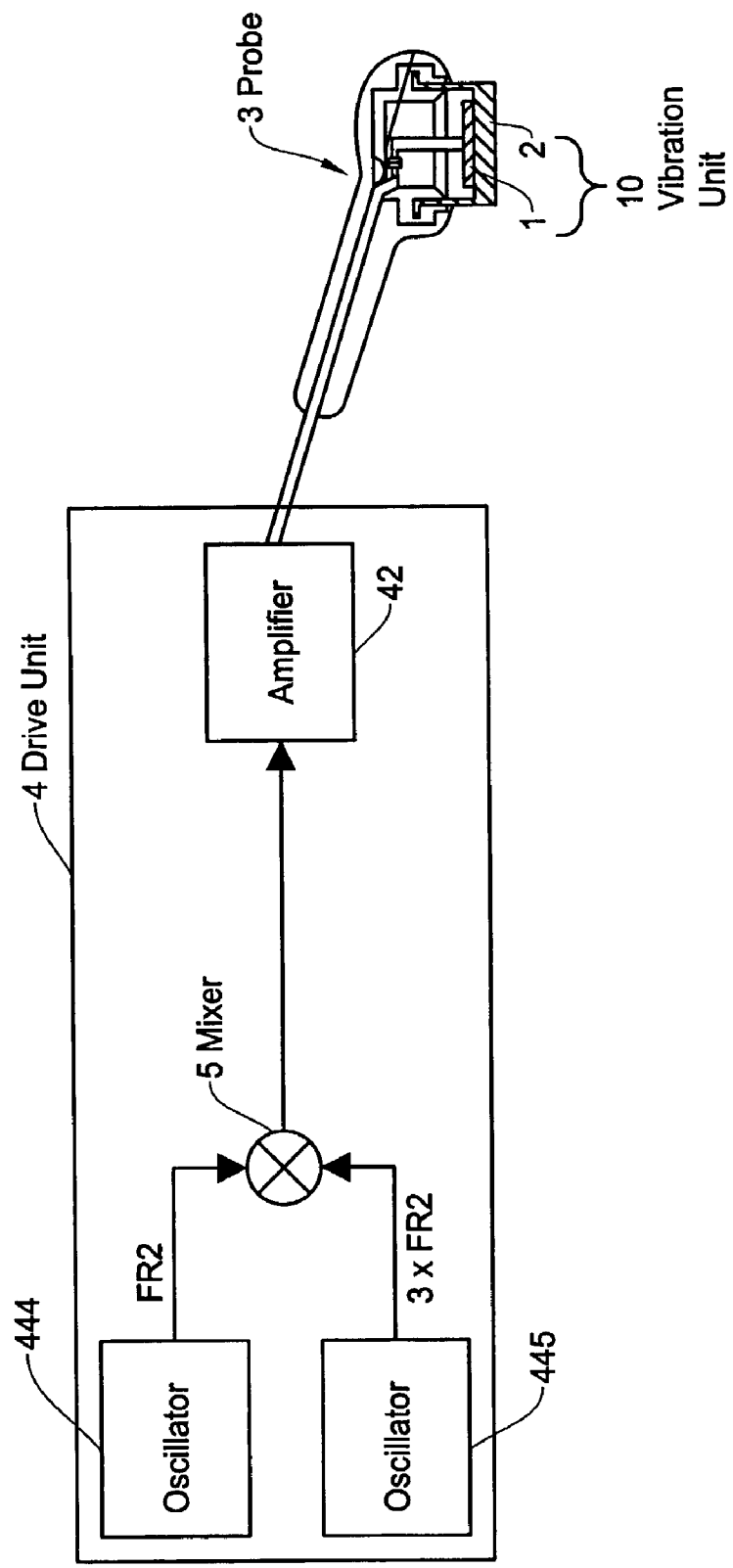
FIG. 16 is a schematic block diagram showing the structure of the ultrasonic wave cosmetic device in the thirteenth embodiment of the present invention.

FIG. 16 is a block diagram showing the structure of the ultrasonic wave cosmetic device related to the thirteenth embodiment of the present invention. The structure of probe 3 is the same as that shown in the first embodiment. The drive unit 4 is comprised of oscillators 444 and 445 for determining the drive frequencies, a frequency mixer 5 for mixing the drive signals from the oscillators 444 and 445, and an amplifier 42 for amplifying the drive signals combined by the mixer 5.

Figure 17:
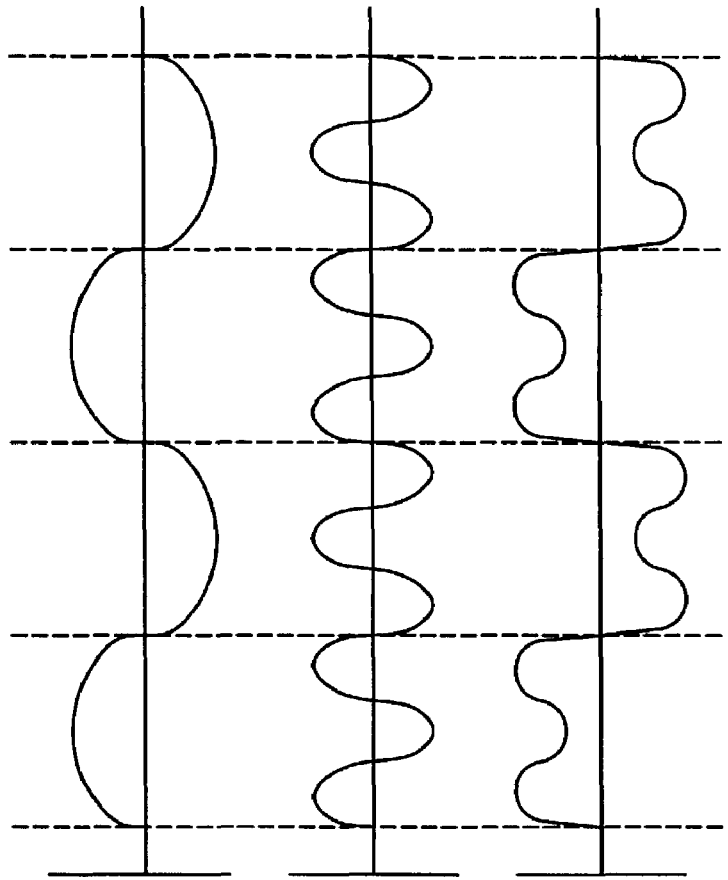
FIGS. 17A–17C are waveform diagrams showing the operation of the ultrasonic wave cosmetic device in the thirteenth embodiment of the present invention.

FIGS. 17A–17C are waveform diagrams for explaining the operational procedure of the ultrasonic wave cosmetic device related to the thirteenth embodiment of the present invention. In the diagram, the horizontal axis represents the time, and the vertical axis represents an output of the oscillator 444 in FIG. 17A, an output of the oscillator 445 in FIG. 17B, and an output of the amplifier 42 (or mixer 5) in FIG. 17C. Here, explanation will be made for the case where the oscillation frequency of the oscillator 444 is the second fundamental frequency FR2 of FIG. 2, and the oscillation frequency of the oscillator 445 is the third harmonic frequency (3×FR2) of FIG. 2.

The outputs of the oscillators 444 and 445 are mixed with each other by the frequency mixer 5 to obtain a frequency combined wave, where the frequency combined wave is then amplified by the amplifier 42. Since the drive unit 4 drives the vibration unit 10 by the use of that frequency mixed wave, the effects based on the plurality of frequencies can be achieved at the same time.

Figure 18:
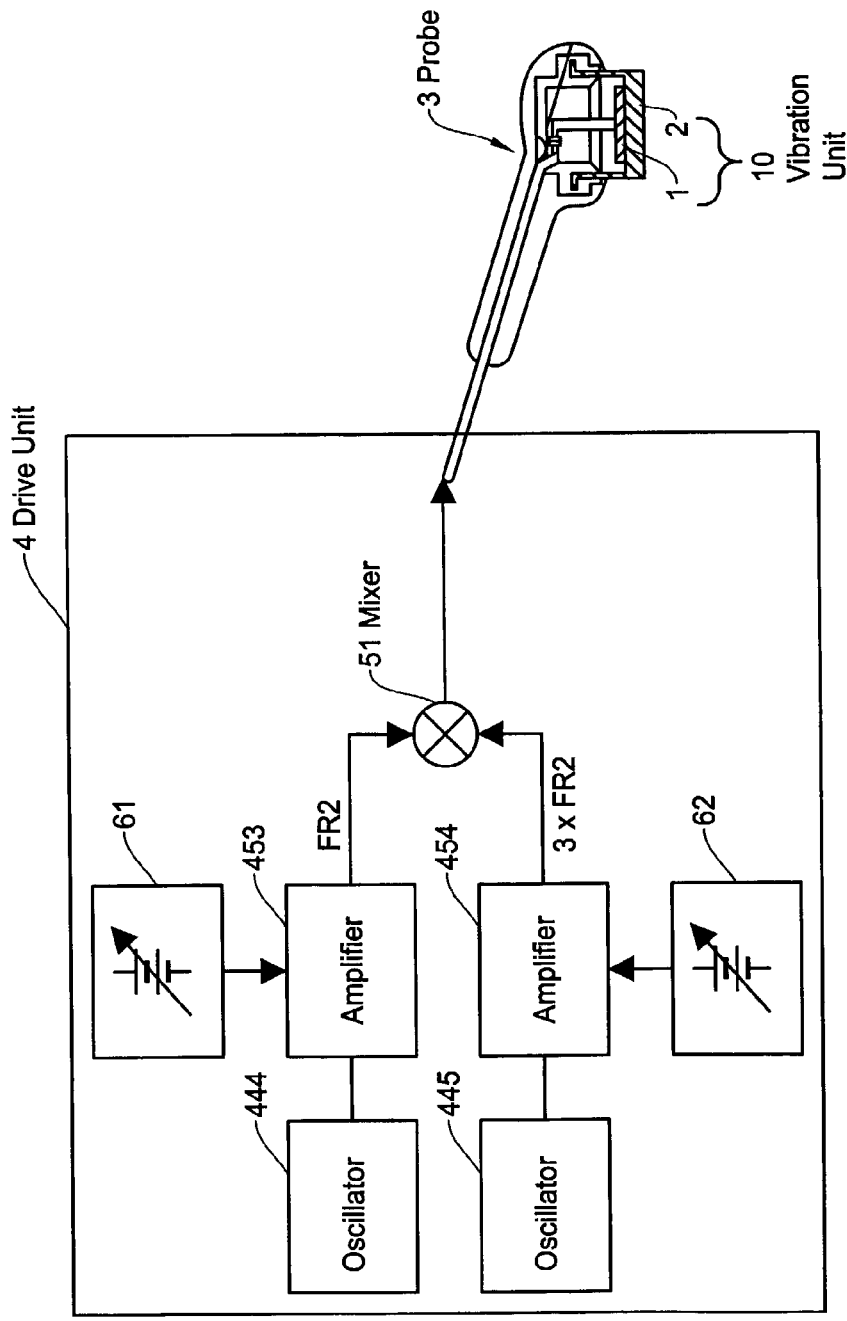
FIG. 18 is a block diagram showing the structure of the ultrasonic wave cosmetic device in the fourteenth embodiment of the present invention.

FIG. 18 is a diagram showing the structure of the ultrasonic wave cosmetic device related to the fourteenth embodiment of the present invention. The structure of the probe 3 is the same as that shown in the first embodiment. The drive unit 4 is comprised of oscillators 444 and 445 for determining the drive frequencies, amplifiers 453 and 454 for amplifying the drive signals from the oscillators 444 and 445, variable voltage power supplies 61 and 62 for controlling a power output of each of the amplifiers 453 and 454, and a frequency mixer 51 for mixing the frequency of the drive signals from the amplifiers 453 and 454.

An output of the oscillator 444 is amplified by the amplifier 453 into a voltage level determined by the variable voltage power source 61, and an output of the oscillator 445 is amplified by the amplifier 454 into a voltage level determined by the variable voltage power source 62. The signals from the amplifiers 453 and 454 are then mixed by the mixer 51.

By the mixer 51, the outputs of oscillators 444 and 445 are mixed to obtain a frequency combined wave which is then amplified by the amplifier 42. Since the drive unit 4 drives the vibration unit 10 by the frequency combined wave, the effects of the plural frequencies can be achieved at the same time.

Since the drive unit 4 includes the variable voltage power sources 61 and 62 and the amplifiers 453 and 454, the output power level of the ultrasonic wave can be set for each frequency.

FIGS. 19A and 19B are block diagrams showing the structure of the ultrasonic wave cosmetic device related to the fifteenth embodiment of the present invention. The structure of the probe 3 is the same as that shown in the first embodiment. The drive unit 4 in FIG. 19A is comprised of an oscillator 7 for determining the drive frequency, an amplifier 81 for amplifying the drive signal from the oscillator 7, and a filter 91 having a predetermined pass-band characteristic and receives the drive signal from the amplifier 81. The drive unit 4 in FIG. 19B is comprised of an oscillator 7 for determining the drive frequency, a filter 91 having a predetermined pass-band characteristic and receives the drive signal from the oscillator 7, and an amplifier 82 for amplifying the drive signal from the filter 92. In this embodiment, it is assumed that the oscillator 7 produces a rectangular wave signal having a predetermined frequency such as the second fundamental frequency FR2 of FIG. 2.

Figure 20A:
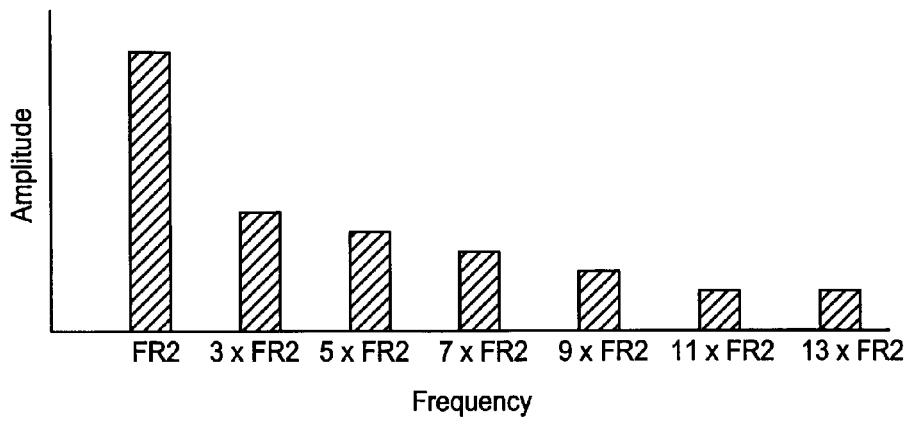
FIGS. 20A–20C are graphs describing the operation of the filter circuit used in the fifteenth embodiment of the present invention.
Figure 20B:
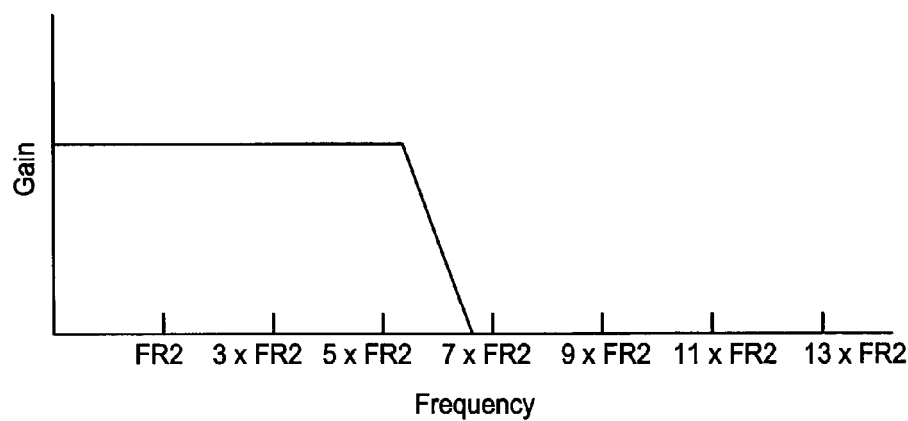
Figure 20C:
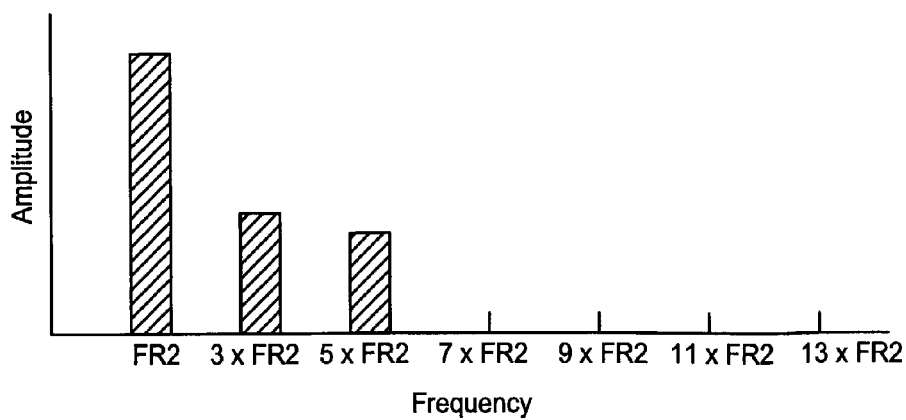

FIGS. 20A–20C are graphs showing the operation of the filter 91 (or 92). FIG. 20A shows rectangular wave frequency spectrum of the second fundamental frequency FR2, FIG. 20B shows an example of a frequency characteristic of the filter 91, and FIG. 20C shows the frequency spectrum at the output of the filter 91 (or 92). The horizontal axis in FIGS. 20A–20C represents the frequency, and the vertical axis in FIGS. 20A and 20C indicates an amplitude, and the vertical axis in FIG. 20B indicates gain.

As shown in FIG. 20A, the rectangular wave is comprised of the second fundamental frequency FR2 as well as harmonics components of odd numbers of FR2. As shown in FIG. 20B, the filter 91 (or 92) has a characteristic which passes the frequency components of FR2, 3×FR2, and 5×FR2, and cuts off the other harmonic components. Therefore, as shown in FIG. 20C, the output of the filter 91 (or 92) includes only the frequency components of FR2, 3×FR2, and 5×FR2.

Since the drive unit 4 includes the filter for adjusting the output level depending on the drive frequency, it is possible to adjust the output level of the ultrasonic wave for each frequency.

FIGS. 21A–21D are cross sectional diagrams showing the vibration unit 10 of the ultrasonic wave cosmetic device related to the sixteenth embodiment of the present invention. The structure other than the vibration unit 10 is the same as that shown in the first embodiment. As shown in FIGS. 21A–21D, the vibration unit 10 is comprised of a plurality of ultrasonic wave vibration elements 11 (or 12) and a horn 2 (or 21).

Figure 21A:
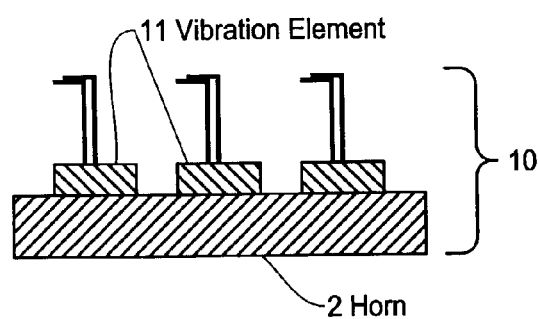
FIGS. 21A–21D are cross sectional views of the vibration unit of the ultrasonic wave cosmetic device in the sixteenth embodiment of the present invention.
Figure 21B:
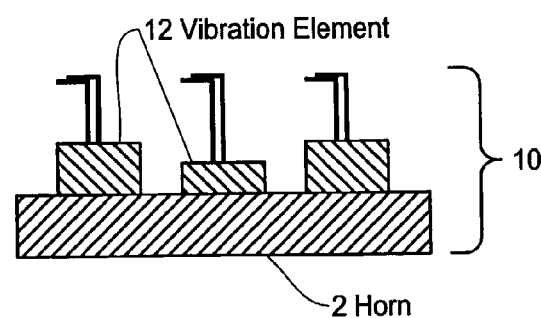
Figure 21C:
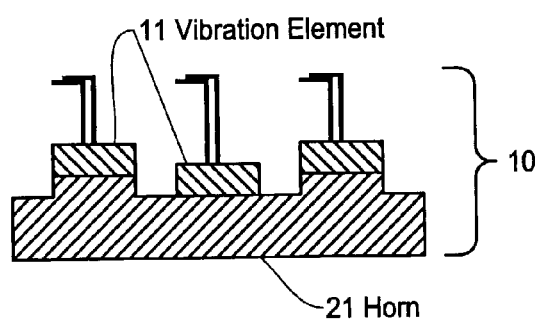
Figure 21D:
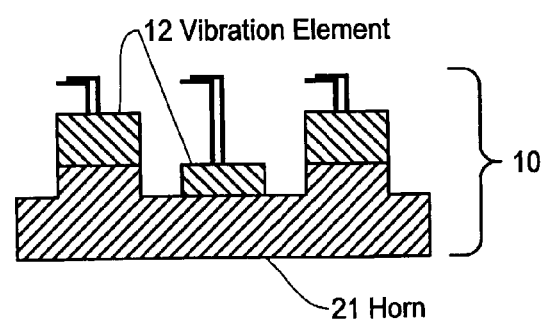

In FIG. 21A, the vibration unit 10 is comprised of ultrasonic wave vibration elements 11 having the same thickness with one another, and a horn 2 having a constant thickness. In FIG. 20B, the vibration unit 10 is comprised of ultrasonic wave vibration elements 12 having different thickness from one another, and a horn 2 having a uniform thickness. In FIG. 20(c), the vibration unit 10 is comprised of ultrasonic wave vibration elements 11 having the same thickness, and a horn 21 having different thickness at which the ultrasonic wave vibration elements 11 are connected. In FIG. 20D, the vibration unit 10 is comprised of ultrasonic wave vibration elements 12 having different thickness from one another, and a horn 2 also having different thickness at which the ultrasonic wave vibration elements 12 are connected.

In either case, since the vibration unit 10 is structured by a plurality of ultrasonic wave vibration elements 11 (or 12) and the horn 2 (or 21), the number of frequencies proportional to the number of ultrasonic wave vibration elements 11 (or 12) can be used, thereby enabling various applications. In this embodiment, the following effects can be achieved by changing the driving method of the ultrasonic wave vibration elements 11 (or 12) through the drive unit 4.

In the case where the plurality of ultrasonic wave vibration elements 11 (or 12) are driven separately, the number of frequencies proportional to the number of the ultrasonic wave vibration elements 11 (or 12) can be used, and thus, various methods of use can be applied.

In the case where the plurality of ultrasonic wave vibration elements 11 (or 12) are driven at the same time, the effects based on the number of frequencies proportional to the number of ultrasonic wave vibration elements 11 (or 12) can be achieved at the same time.

In the case where the plurality of ultrasonic wave vibration elements 11 (or 12) are sequentially switched and driven, the number of frequencies proportional to the number of ultrasonic wave vibration elements 11 (or 12) can be used, and thus, various methods of use can be applied.

As has been described above, the present invention has the following effects:

According to the first aspect of the present invention, since the drive unit produces at least one of the first fundamental frequency and the first harmonic frequency as the drive frequency, it is possible to drive the vibration unit with high frequency as well as with a plurality of frequencies.

According to the second aspect of the present invention, since the drive unit produces at least one of the second fundamental frequency or the second harmonic frequency as the drive frequency, the location of the joint surface between the ultrasonic wave vibration element and the horn aligns with the mid-portions of the standing waves, making the stress applied to the joint surface caused by the vibration substantially zero (=0). Hence, there is almost no energy loss, thereby improving the drive efficiency as well as preventing damages such as breakage of the joint surface.

According to the third aspect of the present invention, since one of either the second fundamental frequency or the third harmonic frequency is used as the drive frequency, the displacement of the ultrasonic wave vibration element between the surface facing the horn and the other surface will be in the opposite directions. Due to this, the ultrasonic wave vibration element will mechanically resonate, further improving the drive efficiency.

According to the fourth aspect of the present invention, since one of the third harmonic frequencies is used as the drive frequency, the structure of the drive unit is simplified, thereby achieving small size and low cost. According to the fifth aspect of the present invention, since the separately excited oscillator is used, the oscillation frequency (drive frequency) becomes adjustable. Due to this, the desired characteristics can be achieved by the adjustment during the production of the ultrasonic wave vibration element and the horn even when the characteristics thereof vary. According to the sixth aspect, since the self-excited oscillator is used, the drive unit with improved drive efficiency can be achieved.

According to seventh aspect of the present invention, since a plurality of frequencies of the second fundamental frequency and the third harmonic frequency can be used as the drive frequencies and the frequency selector is provided to switch the drive frequencies, driving the vibration unit with plural frequencies can be easily done. According to the eighth aspect, since the separately excited oscillator is used, the oscillation frequency (drive frequency) becomes adjustable. Due to this, the desired characteristics can be achieved by the adjustment during the production of the ultrasonic wave vibration element and the horn even when the characteristics thereof vary.

According to the ninth aspect of the present invention, since the self-excited oscillator is used, the drive unit with improved drive efficiency can be achieved. According to the tenth aspect, since the power selector is provided, the output of the ultrasonic wave can be adjusted for each drive frequency. Further, since the transient stress applied to the joint surface between the ultrasonic wave vibration element and the horn generated right after switching the drive frequency can be reduced by decreasing the drive power during the period of switching, the adverse effect of the stress (e.g., breakage of the joint surface) can be reduced.

According to the eleventh aspect of the present invention, since the switching order of the drive frequencies and the drive time for each of the drive frequencies are selected, and the drive frequencies are switched under the control of the condition selector, the plurality of drive frequencies can be used under desired conditions. According to the twelfth aspect, since the time selector selects the stop time during which the drive power of the drive frequency is stopped when the drive frequencies are switched and the frequency controller switches the drive frequencies based on the conditions received from the time selector, the transient stress applied to the joint surface between the ultrasonic wave vibration element and the horn generated right after the drive frequency switch can be reduced. Due to this, it is possible to reduce the effects of the stress (e.g. breakage of the joint surface) and also to prevent the surface of the horn from heating.

According to the thirteenth aspect of the present invention, since the mixed frequency wave is generated by mixing the second fundamental frequency and the third harmonic frequency by the frequency mixer and the drive unit drives the vibration unit by the mixed frequency wave, the effects based on the plurality of frequencies can be achieved at the same time. According to the fourteenth aspect, the output power of the ultrasonic wave can be adjusted for each of the drive frequencies. According to the fifteenth aspect, since the vibration unit is structured with one ultrasonic wave vibration element and one horn, it becomes simple and low cost.

According to the sixteenth aspect of the present invention, since the vibration unit is structured with several ultrasonic wave vibration elements and one horn, the number of frequencies proportional to the number of ultrasonic wave vibration elements can be used, and thus, various methods of use can be applied. According to the seventeenth aspect, since the drive unit drives each of the several ultrasonic wave vibration elements, the number of frequencies proportional to the number of ultrasonic wave vibration elements can be used, and thus, various methods of use can be applied.

According to the eighteenth aspect of the present invention, since the drive unit drives the several ultrasonic wave vibration elements at the same time, the effects based on the number of frequencies proportional to the number of ultrasonic wave vibration elements can be achieved at the same time. According to the nineteenth aspect, since the drive unit sequentially switches and drives the several ultrasonic wave vibration elements, the number of frequencies proportional to the number of ultrasonic wave vibration elements can be used, and thus, various methods of use can be applied.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. An ultrasonic wave cosmetic device for providing ultrasonic stimulation to skin, comprising:
    an ultrasonic wave vibration element for generating ultrasonic waves;
    a probe provided with a vibration unit where one surface of the vibration unit is adapted to contact the skin and another surface is formed of a horn where the vibration unit is configured by the ultrasonic wave vibration element and the horn attached to one another; and
    a drive unit for driving the ultrasonic wave vibration element;
    wherein the drive unit produces at least one of a first fundamental frequency and a first harmonic frequency which is an integer multiple of the first fundamental frequency, as a drive frequency for driving the ultrasonic wave vibration element, where a half-wave length of the fundamental frequency matches a thickness of the vibration unit which is a sum of thickness of the ultrasonic wave vibration element and the horn.

2. An ultrasonic wave cosmetic device as defined in claim 1, wherein the drive unit produces at least one of a second fundamental frequency, where a half-wave length thereof matches the thickness of the ultrasonic wave vibration element and a second harmonic frequency which is an integer multiple of the second fundamental frequency, as a drive frequency for driving the ultrasonic wave vibration element.

3. An ultrasonic wave cosmetic device as defined in claim 2, wherein the drive unit produces at least one of the second fundamental frequency and third harmonic frequencies which are odd multiple of the second fundamental frequency, as a drive frequency for driving the ultrasonic wave vibration element.

4. An ultrasonic wave cosmetic device as defined in claim 3, wherein the drive unit produces one of the third harmonic frequencies as the drive frequency.

5. An ultrasonic wave cosmetic device as defined in claim 3, wherein the drive unit produces a plurality of frequencies of the second fundamental frequency and the third harmonic frequency as the drive frequencies, and has a frequency controller for switching between the plurality of drive frequencies.

6. An ultrasonic wave cosmetic device as defined in claim 5, wherein the drive unit includes a separately excited oscillator for generating the drive frequency.

7. An ultrasonic wave cosmetic device as defined in claim 5, wherein the drive unit includes a self-induced oscillator for generating the drive frequency.

8. An ultrasonic wave cosmetic device as defined in claim 5, wherein the drive unit includes a power controller for controlling a drive power of each of the plurality of drive frequencies.

9. An ultrasonic wave cosmetic device as defined in claim 8, wherein the drive unit includes a condition selector for selecting an switching order of the plurality of drive frequencies and a drive time of each of the drive frequencies; and wherein the frequency controller switches the drive frequencies in response to operations of the condition selector.

10. An ultrasonic wave cosmetic device as defined in claim 9, wherein the drive unit includes a time selector for selecting a stop time during which a drive power of the drive frequency is stopped when the drive frequencies are switched; and wherein the frequency controller switches the drive frequencies in response to operations of the condition selector and the time selector.

11. An ultrasonic wave cosmetic device as defined in claim 3, wherein the drive unit includes a frequency mixer for mixing a plurality of drive frequencies selected from the second fundamental frequency and the third harmonic frequency and for producing a frequency mixed wave which is used as the drive frequency.

12. An ultrasonic wave cosmetic device as defined in claim 11, wherein the drive unit includes output power adjustment means for adjusting an output power of each of the drive frequencies.

13. An ultrasonic wave cosmetic device as defined in claim 1, wherein the drive unit includes a separately excited oscillator for generating the drive frequency.

14. An ultrasonic wave cosmetic device as defined in claim 1, wherein the drive unit includes a self-excited oscillator for generating the drive frequency.

15. An ultrasonic wave cosmetic device as defined in claim 1, wherein the vibration unit is comprised of a single ultrasonic wave vibration element and the horn.

16. An ultrasonic wave cosmetic device as defined in claim 1, wherein the vibration unit is comprised of a plurality of ultrasonic wave vibration elements and the horn.

17. An ultrasonic wave cosmetic device as defined in claim 16, wherein the drive unit drives each of the plurality of ultrasonic wave vibration elements separately.

18. An ultrasonic wave cosmetic device as defined in claim 16, wherein the drive unit drives the plurality of ultrasonic wave vibration elements at the same time.

19. An ultrasonic wave cosmetic device as defined in claim 16, wherein the drive unit sequentially drives the plurality of ultrasonic wave vibration elements by sequentially switching ultrasonic wave vibration elements.

* * * * *